(12) United States Patent
Desborough et al.

(10) Patent No.: US 11,389,088 B2
(45) Date of Patent: Jul. 19, 2022

(54) MULTI-SCALE DISPLAY OF BLOOD GLUCOSE INFORMATION

(71) Applicant: Bigfoot Biomedical, Inc., Milpitas, CA (US)

(72) Inventors: Lane Desborough, Thousand Oaks, CA (US); Bryan Mazlish, Palo Alto, CA (US); Sabine Kabel-Eckes, Mountain View, CA (US); Jeff Boissier, San Jose, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 836 days.

(21) Appl. No.: 16/035,230

(22) Filed: Jul. 13, 2018

(65) Prior Publication Data

US 2019/0015025 A1    Jan. 17, 2019

Related U.S. Application Data

(60) Provisional application No. 62/532,168, filed on Jul. 13, 2017.

(51) Int. Cl.
*A61B 5/145*     (2006.01)
*A61M 5/142*    (2006.01)
(Continued)

(52) U.S. Cl.
CPC ........ *A61B 5/14532* (2013.01); *A61B 5/4839* (2013.01); *A61B 5/6898* (2013.01);
(Continued)

(58) Field of Classification Search
CPC . A61B 5/14532; A61B 5/7435; A61B 5/6898; A61B 5/4839; A61B 5/744;
(Continued)

(56) References Cited

U.S. PATENT DOCUMENTS

| | | |
|---|---|---|
| 2,605,765 A | 8/1952 | Kollsman |
| 3,886,938 A | 6/1975 | Szabo et al. |

(Continued)

FOREIGN PATENT DOCUMENTS

| | | |
|---|---|---|
| CA | 2543545 A1 | 5/2005 |
| DE | 19627619 | 1/1998 |

(Continued)

OTHER PUBLICATIONS

Xilas Temp Touch, "The latest in high-tech and convenient devices," DOCNews, vol. 2, No. 7, Jul. 1, 2005, http://docnews.diabetesjournals.ordlcgi/contenl/foll/2/7i 13, 3 pages.

(Continued)

*Primary Examiner* — Navin Natnithithadha
(74) *Attorney, Agent, or Firm* — TraskBritt

(57) ABSTRACT

A method of displaying blood glucose information may include monitoring blood glucose levels of a user, where the blood glucose levels include at least a current blood glucose level and a historic blood glucose level. The method may also include presenting the current blood glucose level using a point indicator along an approximately horizontally centered axis based on a non-linear scale, and presenting the historic blood glucose level and a predicted future blood glucose level on the display as a single smoothed curve passing the point indicator.

22 Claims, 8 Drawing Sheets

(51) Int. Cl.
*G16H 20/13* (2018.01)
*G16H 40/63* (2018.01)
*A61B 5/00* (2006.01)
*A61M 5/00* (2006.01)
*A61M 5/172* (2006.01)

(52) U.S. Cl.
CPC ............ *A61B 5/744* (2013.01); *A61B 5/7435* (2013.01); *A61M 5/003* (2013.01); *A61M 5/14244* (2013.01); *A61M 5/14248* (2013.01); *A61M 5/1723* (2013.01); *G16H 20/13* (2018.01); *G16H 40/63* (2018.01); *A61B 5/0002* (2013.01); *A61B 5/4836* (2013.01); *A61B 5/7275* (2013.01); *A61M 2005/14272* (2013.01); *A61M 2005/14296* (2013.01); *A61M 2205/505* (2013.01); *A61M 2205/52* (2013.01); *A61M 2230/201* (2013.01)

(58) Field of Classification Search
CPC ... A61B 5/0002; A61B 5/4836; A61B 5/7275; A61M 5/14244; A61M 5/003; A61M 5/14248; A61M 5/1723; A61M 2005/14272; A61M 2005/14296; A61M 2205/505; A61M 2205/52; A61M 2230/201; G16H 20/13; G16H 40/63
USPC .......................................... 600/309, 345–366
See application file for complete search history.

(56) References Cited

U.S. PATENT DOCUMENTS

| | | |
|---|---|---|
| 4,077,405 A | 3/1978 | Haerten et al. |
| 4,231,368 A | 11/1980 | Becker |
| 4,265,241 A | 5/1981 | Portner et al. |
| 4,300,554 A | 11/1981 | Hessberg et al. |
| 4,313,439 A | 2/1982 | Babb et al. |
| 4,398,908 A | 8/1983 | Siposs |
| 4,435,173 A | 3/1984 | Siposs et al. |
| 4,443,218 A | 4/1984 | Decant et al. |
| 4,493,704 A | 1/1985 | Beard et al. |
| 4,529,401 A | 7/1985 | Leslie et al. |
| 4,681,569 A | 7/1987 | Coble et al. |
| 4,749,109 A | 6/1988 | Kamen |
| 4,838,857 A | 6/1989 | Strowe et al. |
| 4,850,817 A | 7/1989 | Nason et al. |
| 5,045,064 A | 9/1991 | Idriss |
| 5,088,981 A | 2/1992 | Howson et al. |
| 5,088,990 A | 2/1992 | Hivale et al. |
| D325,781 S | 4/1992 | Moller-Jensen |
| 5,190,522 A | 3/1993 | Wojcicki et al. |
| 5,225,763 A | 7/1993 | Krohn et al. |
| 5,250,027 A | 10/1993 | Lewis et al. |
| 5,261,882 A | 11/1993 | Sealfon |
| 5,314,412 A | 5/1994 | Rex |
| 5,335,994 A | 8/1994 | Weynant Nee Girones |
| 5,338,157 A | 8/1994 | Blomquist |
| 5,342,180 A | 8/1994 | Daoud |
| D351,469 S | 10/1994 | Okamoto |
| 5,389,078 A | 2/1995 | Zalesky et al. |
| 5,395,340 A | 3/1995 | Lee |
| 5,411,487 A | 5/1995 | Castagna |
| 5,545,143 A | 8/1996 | Fischell et al. |
| 5,551,850 A | 9/1996 | Williamson et al. |
| 5,554,123 A | 9/1996 | Herskowitz |
| 5,569,186 A | 10/1996 | Lord et al. |
| 5,626,566 A | 5/1997 | Petersen et al. |
| 5,637,095 A | 6/1997 | Nason et al. |
| 5,640,954 A | 6/1997 | Pfeiffer et al. |
| 5,665,065 A | 9/1997 | Colman et al. |
| 5,678,571 A | 10/1997 | Brown |
| 5,718,562 A | 2/1998 | Lawless et al. |
| D393,264 S | 4/1998 | Leung |
| 5,741,216 A | 4/1998 | Hemmingsen et al. |
| 5,766,155 A | 6/1998 | Hyman et al. |
| 5,772,635 A | 6/1998 | Dastur et al. |
| 5,816,306 A | 10/1998 | Giacomel |
| 5,822,715 A * | 10/1998 | Worthington .......... A61B 5/411 702/19 |
| 5,852,803 A | 12/1998 | Ashby et al. |
| 5,858,001 A | 1/1999 | Tsals et al. |
| 5,918,603 A | 7/1999 | Brown |
| 5,919,167 A | 7/1999 | Mulhauser et al. |
| 5,925,018 A | 7/1999 | Ungerstedt |
| 5,928,201 A | 7/1999 | Poulsen et al. |
| 5,947,934 A | 9/1999 | Hansen et al. |
| 5,951,530 A | 9/1999 | Steengaard et al. |
| 5,957,889 A | 9/1999 | Poulsen et al. |
| 5,984,894 A | 11/1999 | Poulsen et al. |
| 5,984,897 A | 11/1999 | Petersen et al. |
| 5,997,475 A | 12/1999 | Bortz |
| 6,003,736 A | 12/1999 | Ljunggren |
| 6,010,485 A | 1/2000 | Buch-Rasmussen et al. |
| 6,032,119 A | 2/2000 | Brown et al. |
| 6,033,377 A | 3/2000 | Rasmussen et al. |
| 6,045,537 A | 4/2000 | Klitmose |
| D424,036 S | 5/2000 | Arora et al. |
| 6,056,728 A | 5/2000 | Von Schuckmann |
| 6,074,372 A | 6/2000 | Hansen |
| 6,110,149 A | 8/2000 | Klitgaard et al. |
| 6,156,014 A | 12/2000 | Petersen et al. |
| 6,171,276 B1 | 1/2001 | Lippe et al. |
| 6,231,540 B1 | 5/2001 | Smedegaard |
| 6,248,067 B1 | 6/2001 | Causey et al. |
| 6,248,090 B1 | 6/2001 | Jensen et al. |
| 6,248,093 B1 | 6/2001 | Moberg |
| 6,277,098 B1 | 8/2001 | Klitmose et al. |
| 6,302,855 B1 | 10/2001 | Lav et al. |
| 6,302,869 B1 | 10/2001 | Klitgaard |
| 6,354,996 B1 | 3/2002 | Drinan et al. |
| 6,368,314 B1 | 4/2002 | Kipfer et al. |
| 6,375,638 B2 | 4/2002 | Nason et al. |
| 6,379,301 B1 * | 4/2002 | Worthington ........ A61B 5/7275 600/309 |
| 6,379,339 B1 | 4/2002 | Klitgaard et al. |
| 6,381,496 B1 | 4/2002 | Meadows et al. |
| 6,404,098 B1 | 6/2002 | Kayama et al. |
| D460,053 S | 7/2002 | Choi |
| 6,427,088 B1 | 7/2002 | Bowman et al. |
| D461,241 S | 8/2002 | Moberg et al. |
| D461,891 S | 8/2002 | Moberg |
| 6,436,072 B1 | 8/2002 | Kullas et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,589,229 B1 | 7/2003 | Connelly et al. |
| 6,605,067 B1 | 8/2003 | Larsen |
| 6,613,019 B2 | 9/2003 | Munk |
| 6,641,533 B2 | 11/2003 | Causey et al. |
| 6,648,821 B2 | 11/2003 | Lebel et al. |
| 6,650,951 B1 | 11/2003 | Jones et al. |
| 6,656,158 B2 | 12/2003 | Mahoney et al. |

(56) References Cited

U.S. PATENT DOCUMENTS

| | | |
|---|---|---|
| 6,656,159 B2 | 12/2003 | Flaherty |
| 6,659,948 B2 | 12/2003 | Lebel et al. |
| 6,659,978 B1 | 12/2003 | Kasuga et al. |
| 6,659,980 B2 | 12/2003 | Moberg et al. |
| 6,663,602 B2 | 12/2003 | Moeller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman et al. |
| 6,956,572 B2 | 10/2005 | Zaleski |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van et al. |
| 7,008,399 B2 | 3/2006 | Larsen et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,096,431 B2 | 8/2006 | Tambata et al. |
| 7,104,972 B2 | 9/2006 | Moller et al. |
| 7,109,878 B2 | 9/2006 | Mann et al. |
| 7,128,727 B2 | 10/2006 | Flaherty et al. |
| 7,133,329 B2 | 11/2006 | Skyggebjerg et al. |
| 7,232,423 B2 | 6/2007 | Mernoee |
| D545,837 S | 7/2007 | Haldimann et al. |
| 7,241,265 B2 | 7/2007 | Cummings et al. |
| D550,227 S | 9/2007 | Sato et al. |
| D554,140 S | 10/2007 | Armendariz |
| 7,291,107 B2 | 11/2007 | Hellwig et al. |
| 7,343,197 B2 | 3/2008 | Shusterman |
| 7,440,786 B2 * | 10/2008 | Hockersmith ......... G16H 15/00 600/316 |
| 7,454,359 B2 | 11/2008 | Rosenfeld et al. |
| D592,223 S | 5/2009 | Neuhaus |
| 7,534,226 B2 | 5/2009 | Mernoe et al. |
| 7,553,281 B2 | 6/2009 | Hellwig et al. |
| 7,570,980 B2 | 8/2009 | Ginsberg |
| D600,341 S | 9/2009 | Loerwald |
| D603,421 S | 11/2009 | Ebeling et al. |
| D607,099 S | 12/2009 | Loerwald |
| 7,647,237 B2 | 1/2010 | Malave et al. |
| D614,587 S | 4/2010 | Yodfat et al. |
| 7,695,434 B2 | 4/2010 | Malecha |
| 7,708,717 B2 | 5/2010 | Estes et al. |
| 7,717,903 B2 | 5/2010 | Estes et al. |
| 7,751,907 B2 | 7/2010 | Blomquist |
| D623,753 S | 9/2010 | Saffer et al. |
| 7,789,859 B2 | 9/2010 | Estes et al. |
| 7,828,528 B2 | 11/2010 | Estes et al. |
| 7,837,647 B2 | 11/2010 | Estes et al. |
| 7,850,641 B2 | 12/2010 | Lebel et al. |
| 7,871,376 B2 | 1/2011 | Brown |
| 7,878,975 B2 | 2/2011 | Liljeryd et al. |
| 7,887,512 B2 | 2/2011 | Estes et al. |
| 7,931,613 B2 | 4/2011 | Haueter et al. |
| 7,938,797 B2 | 5/2011 | Estes |
| D640,269 S | 6/2011 | Chen |
| D642,191 S | 7/2011 | Barnett et al. |
| 8,012,119 B2 | 9/2011 | Estes et al. |
| D652,426 S | 1/2012 | Anzures |
| 8,132,101 B2 | 3/2012 | Buck et al. |
| RE43,316 E * | 4/2012 | Brown ............... A61B 5/6896 600/309 |
| D656,950 S | 4/2012 | Shallcross et al. |
| 8,156,070 B2 | 4/2012 | Buck et al. |
| D660,315 S | 5/2012 | Anzures |
| D661,701 S | 6/2012 | Brown et al. |
| 8,202,249 B2 | 6/2012 | Iio et al. |
| 8,217,946 B2 | 7/2012 | Halpern et al. |
| 8,219,222 B2 | 7/2012 | Blomquist |
| 8,221,345 B2 | 7/2012 | Blomquist |
| 8,231,562 B2 | 7/2012 | Buck et al. |
| D665,409 S | 8/2012 | Gupta et al. |
| 8,237,715 B2 | 8/2012 | Buck et al. |
| 8,250,483 B2 | 8/2012 | Blomquist |
| 8,257,652 B2 | 9/2012 | Drucker et al. |
| 8,257,653 B2 | 9/2012 | Drucker et al. |
| 8,262,616 B2 | 9/2012 | Grant et al. |
| 8,273,296 B2 | 9/2012 | Drucker et al. |
| D669,165 S | 10/2012 | Estes et al. |
| D669,166 S | 10/2012 | Estes et al. |
| D669,167 S | 10/2012 | Estes et al. |
| 8,279,226 B2 | 10/2012 | Krieftewirth |
| 8,310,415 B2 | 11/2012 | McLaughlin et al. |
| 8,337,469 B2 | 12/2012 | Eberhart et al. |
| 8,357,091 B2 | 1/2013 | Say et al. |
| 8,365,065 B2 | 1/2013 | Gejdos et al. |
| 8,372,005 B2 | 2/2013 | Say et al. |
| D682,289 S | 5/2013 | Dijulio et al. |
| 8,439,834 B2 | 5/2013 | Schmelzeisen-Redeker et al. |
| D683,738 S | 6/2013 | Wujcik et al. |
| D687,541 S | 8/2013 | Estes et al. |
| 8,514,086 B2 | 8/2013 | Harper et al. |
| D689,523 S | 9/2013 | Galbraith et al. |
| D689,874 S | 9/2013 | Brinda et al. |
| 8,529,838 B2 | 9/2013 | Drucker et al. |
| 8,529,839 B2 | 9/2013 | Drucker et al. |
| 8,529,841 B2 | 9/2013 | Drucker et al. |
| D691,258 S | 10/2013 | Estes et al. |
| D691,259 S | 10/2013 | Estes et al. |
| D693,114 S | 11/2013 | Lemanski, Sr. |
| 8,579,815 B2 | 11/2013 | Galley et al. |
| 8,601,005 B2 | 12/2013 | Bousamra et al. |
| 8,615,366 B2 | 12/2013 | Galley et al. |

(56) References Cited

U.S. PATENT DOCUMENTS

| | | |
|---|---|---|
| D697,204 S | 1/2014 | Maier et al. |
| 8,622,906 B2 | 1/2014 | Say et al. |
| D699,741 S | 2/2014 | Wantland et al. |
| 8,657,779 B2 | 2/2014 | Blomquist |
| D701,879 S | 4/2014 | Foit et al. |
| D702,258 S | 4/2014 | Wantland et al. |
| 8,719,945 B2 | 5/2014 | Birtwhistle et al. |
| 8,756,074 B2 | 6/2014 | Brzustowicz |
| 8,761,940 B2 | 6/2014 | Long et al. |
| D709,183 S | 7/2014 | Kemlein |
| 8,774,887 B2 | 7/2014 | Say et al. |
| 8,816,862 B2 | 8/2014 | Harper et al. |
| 8,839,106 B2 | 9/2014 | Lee et al. |
| D714,816 S | 10/2014 | Varon |
| D715,835 S | 10/2014 | Montgomery et al. |
| D717,822 S | 11/2014 | Brotman et al. |
| D717,830 S | 11/2014 | Brinda et al. |
| D718,438 S | 11/2014 | Davis et al. |
| 8,895,315 B2 | 11/2014 | Batman et al. |
| D719,186 S | 12/2014 | Kim |
| 8,961,465 B2 | 2/2015 | Blomquist |
| D727,336 S | 4/2015 | Allison et al. |
| 9,008,803 B2 | 4/2015 | Blomquist |
| 9,022,996 B2 | 5/2015 | Eberhart et al. |
| 9,033,877 B2 | 5/2015 | Werner et al. |
| 9,041,730 B2 | 5/2015 | Johnson et al. |
| D733,175 S | 6/2015 | Bae |
| D733,179 S | 6/2015 | Kwon |
| 9,050,409 B2 | 6/2015 | Haueter et al. |
| 9,072,477 B2 | 7/2015 | Say et al. |
| 9,076,107 B2 | 7/2015 | Cameron et al. |
| D736,792 S | 8/2015 | Brinda et al. |
| D737,278 S | 8/2015 | Shin et al. |
| D738,907 S | 9/2015 | Cabrera-Cordon et al. |
| D738,913 S | 9/2015 | Cabrera-Cordon et al. |
| D738,914 S | 9/2015 | Torres et al. |
| 9,134,823 B2 | 9/2015 | Grant et al. |
| 9,136,939 B2 | 9/2015 | Galley et al. |
| 9,159,148 B2 | 10/2015 | Boyer et al. |
| D743,435 S | 11/2015 | Herold et al. |
| 9,186,113 B2 | 11/2015 | Harper et al. |
| D744,505 S | 12/2015 | Wilberding et al. |
| D745,050 S | 12/2015 | Kwon |
| 9,198,623 B2 | 12/2015 | Fern et al. |
| D751,585 S | 3/2016 | Kaufthal et al. |
| D751,586 S | 3/2016 | Kaufthal et al. |
| D752,736 S | 3/2016 | Chandrasenan et al. |
| D755,830 S | 5/2016 | Chaudhri et al. |
| D757,026 S | 5/2016 | Lim et al. |
| D757,047 S | 5/2016 | Cornwell et al. |
| 9,336,355 B2 * | 5/2016 | Ljuhs ................... A61B 5/7275 |
| D763,860 S | 8/2016 | Sunshine et al. |
| D766,424 S | 9/2016 | Anderson et al. |
| D768,144 S | 10/2016 | Kim et al. |
| D768,687 S | 10/2016 | Bae et al. |
| D769,322 S | 10/2016 | Rajeswaran et al. |
| D772,924 S | 11/2016 | Begin et al. |
| 9,498,164 B2 * | 11/2016 | Johnson ............... A61B 5/0013 |
| 9,498,165 B2 * | 11/2016 | Johnson ............... A61B 5/1495 |
| 9,504,430 B2 * | 11/2016 | Johnson ................. G06T 11/20 |
| D776,253 S | 1/2017 | Li |
| D777,906 S | 1/2017 | Anderson et al. |
| D781,305 S | 3/2017 | Lau |
| D781,908 S | 3/2017 | Bhandari et al. |
| D786,266 S | 5/2017 | Van et al. |
| D786,270 S | 5/2017 | Barry et al. |
| D788,145 S | 5/2017 | Sullivan et al. |
| 9,707,336 B2 | 7/2017 | Dang et al. |
| D795,284 S | 8/2017 | Miller et al. |
| 9,717,849 B2 | 8/2017 | Mhatre et al. |
| D797,771 S | 9/2017 | Caporal et al. |
| D800,757 S | 10/2017 | Mullen et al. |
| D801,519 S | 10/2017 | Sabin et al. |
| 9,833,199 B2 * | 12/2017 | Johnson ..................... G06T 3/00 |
| D806,748 S | 1/2018 | Van et al. |
| D806,749 S | 1/2018 | Van et al. |
| D806,750 S | 1/2018 | Van et al. |
| D809,134 S | 1/2018 | Crothall |
| 9,878,097 B2 | 1/2018 | Estes |
| 9,931,454 B2 | 4/2018 | Lo et al. |
| 10,154,804 B2 * | 12/2018 | Steil ..................... A61M 5/1723 |
| 10,165,986 B2 * | 1/2019 | Johnson ............. G06F 3/04883 |
| 10,265,030 B2 * | 4/2019 | Johnson ................. A61B 5/743 |
| 10,278,650 B2 * | 5/2019 | Johnson ............... A61B 5/7445 |
| 10,426,896 B2 * | 10/2019 | Desborough ....... A61M 5/3202 |
| 2001/0041869 A1 | 11/2001 | Causey et al. |
| 2001/0056262 A1 | 12/2001 | Cabiri et al. |
| 2002/0004651 A1 | 1/2002 | Ljunggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2002/0177810 A1 | 11/2002 | Reilly et al. |
| 2003/0055380 A1 | 3/2003 | Flaherty |
| 2003/0065308 A1 | 4/2003 | Lebel et al. |
| 2003/0088238 A1 | 5/2003 | Poulsen et al. |
| 2003/0167035 A1 | 9/2003 | Flaherty et al. |
| 2003/0198558 A1 | 10/2003 | Nason et al. |
| 2003/0199825 A1 | 10/2003 | Flaherty |
| 2003/0208113 A1 * | 11/2003 | Mault ................. A61B 5/14532 <br> 600/316 |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0093331 A1 | 5/2004 | Garner et al. |
| 2004/0116866 A1 | 6/2004 | Gorman et al. |
| 2004/0127844 A1 | 7/2004 | Flaherty |
| 2004/0153032 A1 | 8/2004 | Garibotto et al. |
| 2004/0153257 A1 | 8/2004 | Munk |
| 2004/0171983 A1 | 9/2004 | Sparks et al. |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0037482 A1 | 2/2005 | Braig et al. |
| 2005/0065760 A1 | 3/2005 | Murtfeldt et al. |
| 2005/0090808 A1 | 4/2005 | Malave et al. |
| 2005/0090851 A1 | 4/2005 | Devlin |
| 2005/0095063 A1 | 5/2005 | Fathallah et al. |
| 2005/0159656 A1 * | 7/2005 | Hockersmith ......... G16H 15/00 <br> 600/315 |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192494 A1 | 9/2005 | Ginsberg |
| 2005/0192561 A1 | 9/2005 | Mernoe |
| 2005/0203461 A1 | 9/2005 | Flaherty et al. |
| 2005/0209515 A1 * | 9/2005 | Hockersmith ....... A61B 5/7475 <br> 600/316 |
| 2005/0215982 A1 | 9/2005 | Malave et al. |
| 2005/0222645 A1 | 10/2005 | Malave et al. |
| 2005/0234404 A1 | 10/2005 | Vilks et al. |
| 2005/0238507 A1 | 10/2005 | Diianni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0095014 A1 | 5/2006 | Ethelfeld |
| 2006/0135913 A1 | 6/2006 | Ethelfeld |
| 2006/0142698 A1 | 6/2006 | Ethelfeld |
| 2006/0151545 A1 | 7/2006 | Imhof et al. |
| 2006/0178633 A1 | 8/2006 | Garibotto et al. |

(56) References Cited

U.S. PATENT DOCUMENTS

| | | |
|---|---|---|
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0088271 A1 | 4/2007 | Richards |
| 2007/0106218 A1 | 5/2007 | Yodfat et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0179444 A1 | 8/2007 | Causey et al. |
| 2007/0239116 A1 | 10/2007 | Follman et al. |
| 2008/0033254 A1* | 2/2008 | Kamath ............... A61B 5/743 600/300 |
| 2008/0051716 A1 | 2/2008 | Stutz |
| 2008/0097381 A1 | 4/2008 | Moberg et al. |
| 2008/0119705 A1 | 5/2008 | Patel et al. |
| 2008/0208627 A1 | 8/2008 | Skyggebjerg |
| 2008/0287755 A1 | 11/2008 | Sass et al. |
| 2008/0294094 A1 | 11/2008 | Mhatre et al. |
| 2008/0294108 A1 | 11/2008 | Briones et al. |
| 2008/0294109 A1 | 11/2008 | Estes et al. |
| 2008/0294142 A1 | 11/2008 | Patel et al. |
| 2008/0300572 A1* | 12/2008 | Rankers ............... G16H 15/00 604/504 |
| 2008/0319383 A1 | 12/2008 | Byland et al. |
| 2009/0067989 A1 | 3/2009 | Estes et al. |
| 2009/0069745 A1 | 3/2009 | Estes et al. |
| 2009/0069746 A1 | 3/2009 | Miller et al. |
| 2009/0069749 A1 | 3/2009 | Miller et al. |
| 2009/0069784 A1 | 3/2009 | Estes et al. |
| 2009/0069785 A1 | 3/2009 | Miller et al. |
| 2009/0069787 A1 | 3/2009 | Estes et al. |
| 2009/0099523 A1 | 4/2009 | Grant et al. |
| 2009/0156990 A1 | 6/2009 | Wenger et al. |
| 2009/0292247 A1 | 11/2009 | Basso et al. |
| 2010/0010330 A1* | 1/2010 | Rankers ............... A61B 5/411 600/365 |
| 2010/0075353 A1* | 3/2010 | Heaton ............... G16H 20/60 435/14 |
| 2010/0280329 A1 | 11/2010 | Randloev et al. |
| 2010/0305965 A1 | 12/2010 | Benjamin et al. |
| 2011/0009846 A1 | 1/2011 | Istoc et al. |
| 2011/0040247 A1 | 2/2011 | Mandro et al. |
| 2011/0160555 A1 | 6/2011 | Reifman et al. |
| 2011/0201911 A1* | 8/2011 | Johnson ............... G06F 3/041 600/365 |
| 2012/0022496 A1 | 1/2012 | Causey et al. |
| 2012/0053560 A1 | 3/2012 | Kawamura |
| 2012/0203166 A1* | 8/2012 | Riback ............... G16H 50/30 604/66 |
| 2012/0203467 A1* | 8/2012 | Kamath ............... A61B 5/14542 702/19 |
| 2012/0209091 A1* | 8/2012 | Riback ............... G16H 40/63 600/309 |
| 2012/0209099 A1* | 8/2012 | Ljuhs ............... A61B 5/4839 600/365 |
| 2012/0215086 A1* | 8/2012 | Kamath ............... A61B 5/7203 600/365 |
| 2012/0215201 A1 | 8/2012 | Brauker et al. |
| 2012/0215496 A1* | 8/2012 | Kamath ............... A61B 5/14542 702/191 |
| 2012/0238999 A1 | 9/2012 | Estes et al. |
| 2012/0245855 A1* | 9/2012 | Kamath ............... A61B 5/01 702/19 |
| 2012/0323100 A1* | 12/2012 | Kamath ............... A61B 5/14532 600/365 |
| 2012/0330270 A1 | 12/2012 | Colton |
| 2013/0172710 A1 | 7/2013 | Mears et al. |
| 2013/0324941 A1 | 12/2013 | Mann et al. |
| 2013/0331659 A1 | 12/2013 | Koski et al. |
| 2013/0338453 A1 | 12/2013 | Duke et al. |
| 2014/0025400 A1 | 1/2014 | Galley et al. |
| 2014/0039383 A1 | 2/2014 | Dobbles et al. |
| 2014/0058749 A1 | 2/2014 | Galley et al. |
| 2014/0068487 A1 | 3/2014 | Steiger et al. |
| 2014/0073892 A1 | 3/2014 | Randloev et al. |
| 2014/0091940 A1* | 4/2014 | Johnson ............... A61B 5/743 340/815.4 |
| 2014/0091941 A1* | 4/2014 | Johnson ............... G01N 33/66 340/815.4 |
| 2014/0094673 A1* | 4/2014 | Johnson ............... H04N 21/431 600/365 |
| 2014/0128705 A1* | 5/2014 | Mazlish ............... A61B 5/14532 600/365 |
| 2014/0317546 A1 | 10/2014 | Jacobson et al. |
| 2014/0344280 A1 | 11/2014 | Wei et al. |
| 2014/0358082 A1 | 12/2014 | Ohzawa |
| 2014/0380218 A1 | 12/2014 | Johnnie |
| 2015/0025498 A1 | 1/2015 | Estes |
| 2015/0073337 A1 | 3/2015 | Saint et al. |
| 2015/0080842 A1 | 3/2015 | Mathys |
| 2015/0112264 A1 | 4/2015 | Kamen et al. |
| 2015/0141912 A1 | 5/2015 | Estes |
| 2015/0173674 A1 | 6/2015 | Hayes et al. |
| 2015/0227710 A1 | 8/2015 | Pappada |
| 2015/0253334 A1* | 9/2015 | Johnson ............... A61B 5/1495 702/182 |
| 2015/0277722 A1 | 10/2015 | Masterson et al. |
| 2015/0289819 A1* | 10/2015 | Kamath ............... A61B 5/14865 600/365 |
| 2016/0000998 A1 | 1/2016 | Estes |
| 2016/0038675 A1 | 2/2016 | Estes et al. |
| 2016/0058939 A1 | 3/2016 | Brewer et al. |
| 2016/0072841 A1 | 3/2016 | Caporal et al. |
| 2016/0089491 A1 | 3/2016 | Smith |
| 2016/0100807 A1* | 4/2016 | Johnson ............... A61B 5/1495 340/870.07 |
| 2016/0103604 A1* | 4/2016 | Johnson ............... A61B 5/7475 715/772 |
| 2016/0193411 A1* | 7/2016 | Ljuhs ............... G16H 50/20 604/504 |
| 2016/0235913 A1 | 8/2016 | Smith et al. |
| 2016/0250422 A1 | 9/2016 | Koch et al. |
| 2016/0361494 A1 | 12/2016 | Rg et al. |
| 2017/0003848 A1 | 1/2017 | Wakayanagi et al. |
| 2017/0042487 A1* | 2/2017 | Johnson ............... G06F 3/04883 |
| 2017/0049957 A1 | 2/2017 | Michaud |
| 2017/0100538 A1 | 4/2017 | Mhatre et al. |
| 2017/0128021 A1* | 5/2017 | Kamath ............... A61B 5/742 |
| 2017/0128023 A1* | 5/2017 | Riback ............... G16H 50/20 |
| 2017/0181629 A1* | 6/2017 | Mahalingam ...... A61B 5/14532 |
| 2017/0181630 A1* | 6/2017 | Mahalingam ........ A61B 5/0022 |
| 2017/0181645 A1* | 6/2017 | Mahalingam ...... A61B 5/14532 |
| 2017/0189614 A1 | 7/2017 | Mazlish et al. |
| 2017/0199985 A1 | 7/2017 | Mazlish et al. |
| 2017/0203030 A1 | 7/2017 | Brewer et al. |
| 2017/0203036 A1 | 7/2017 | Mazlish et al. |
| 2017/0203037 A1 | 7/2017 | Desborough et al. |
| 2017/0203038 A1 | 7/2017 | Desborough et al. |
| 2017/0203039 A1 | 7/2017 | Desborough et al. |
| 2017/0224910 A1 | 8/2017 | Yodfat et al. |
| 2017/0232195 A1 | 8/2017 | Desborough et al. |
| 2017/0242975 A1 | 8/2017 | Kahlbaugh |
| 2017/0316592 A1 | 11/2017 | Kamath et al. |
| 2017/0332952 A1 | 11/2017 | Desborough et al. |
| 2018/0001006 A1 | 1/2018 | Schade et al. |
| 2018/0042558 A1* | 2/2018 | Cabrera, Jr ......... A61B 5/7275 |
| 2018/0042559 A1* | 2/2018 | Cabrera, Jr ......... G06F 3/04847 |
| 2018/0085532 A1* | 3/2018 | Desborough ....... G06F 19/3468 |
| 2018/0116589 A1* | 5/2018 | Mazlish ............... A61B 5/743 |
| 2018/0133397 A1 | 5/2018 | Estes |
| 2018/0150614 A1 | 5/2018 | Sokolovskyy et al. |
| 2018/0161499 A1 | 6/2018 | Al-Ali et al. |
| 2018/0200435 A1 | 7/2018 | Mazlish et al. |
| 2018/0200436 A1 | 7/2018 | Mazlish et al. |
| 2018/0200437 A1 | 7/2018 | Mazlish et al. |
| 2018/0200438 A1 | 7/2018 | Mazlish et al. |
| 2018/0200439 A1 | 7/2018 | Mazlish et al. |

(56) References Cited

U.S. PATENT DOCUMENTS

| | | | |
|---|---|---|---|
| 2018/0200441 A1 | | 7/2018 | Desborough et al. |
| 2018/0207380 A1 | | 7/2018 | Lantz et al. |
| 2018/0217917 A1 | | 8/2018 | Hayter et al. |
| 2018/0279959 A1* | 10/2018 | Kamath | A61B 5/726 |
| 2018/0289333 A1* | 10/2018 | Kamath | A61B 5/1495 |
| 2019/0015024 A1 | | 1/2019 | Desborough et al. |

FOREIGN PATENT DOCUMENTS

| | | |
|---|---|---|
| DE | 10236669 A1 | 2/2004 |
| EM | 0006276170001 | 1/2007 |
| EM | 0006276170002 | 1/2007 |
| EM | 0006276170003 | 1/2007 |
| EM | 0007326490001 | 6/2007 |
| EM | 0007326490002 | 6/2007 |
| EM | 0031267050001 | 7/2016 |
| EM | 0031267050002 | 7/2016 |
| EM | 0031267050003 | 7/2016 |
| EM | 0031267050004 | 7/2016 |
| EP | 0062974 A1 | 10/1982 |
| EP | 0275213 A2 | 7/1988 |
| EP | 0496141 A1 | 7/1992 |
| EP | 0580723 A1 | 2/1994 |
| EP | 0612004 A1 | 8/1994 |
| EP | 0721358 A1 | 7/1996 |
| EP | 1045146 A2 | 10/2000 |
| EP | 1136698 A1 | 9/2001 |
| EP | 1177802 A1 | 2/2002 |
| EP | 1495775 A1 | 1/2005 |
| EP | 1527792 A1 | 5/2005 |
| EP | 1754498 A1 | 2/2007 |
| EP | 1818664 A1 | 8/2007 |
| EP | 2500049 A1 | 9/2012 |
| FR | 2585252 A1 | 1/1987 |
| GB | 0747701 | 4/1956 |
| GB | 2218831 A | 11/1989 |
| JP | 2014-145594 A | 8/2014 |
| WO | 90/15928 A1 | 12/1990 |
| WO | 95/09021 A1 | 4/1995 |
| WO | 97/21457 A1 | 6/1997 |
| WO | 98/04301 A1 | 2/1998 |
| WO | 98/11927 A1 | 3/1998 |
| WO | 98/57683 A1 | 12/1998 |
| WO | 99/21596 A1 | 5/1999 |
| WO | 99/39118 A1 | 8/1999 |
| WO | 99/48546 A1 | 9/1999 |
| WO | 01/72360 A1 | 10/2001 |
| WO | 01/91822 A1 | 12/2001 |
| WO | 01/91833 A1 | 12/2001 |
| WO | 02/40083 A2 | 5/2002 |
| WO | 02/57627 A1 | 7/2002 |
| WO | 02/68015 A2 | 9/2002 |
| WO | 02/84336 A2 | 10/2002 |
| WO | 2002/100469 A2 | 12/2002 |
| WO | 03/26726 A1 | 4/2003 |
| WO | 2003/103763 A1 | 12/2003 |
| WO | 2004/056412 A2 | 7/2004 |
| WO | 2004/110526 A1 | 12/2004 |
| WO | 2005/002652 A2 | 1/2005 |
| WO | 2005/039673 A2 | 5/2005 |
| WO | 2005/072794 A2 | 8/2005 |
| WO | 2005/072795 A2 | 8/2005 |
| WO | 2006/067217 A2 | 6/2006 |
| WO | 2006/097453 A1 | 9/2006 |
| WO | 2006/105792 A1 | 10/2006 |
| WO | 2006/105793 A1 | 10/2006 |
| WO | 2006/105794 A1 | 10/2006 |
| WO | 2007/141786 A1 | 12/2007 |
| WO | 2011/163450 A1 | 12/2011 |
| WO | 2018/111928 A1 | 6/2018 |

OTHER PUBLICATIONS

The Medtronic Diabetes Connection, 2006, 6 pages.
T:slimx2 Insulin Pump User Guide, Tandem Diabetes Care, Jul. 22, 2016.
Sara Krugman, Bionic Pancreas User Interface (3/4): Interface Details, Tidepool.org, Jul. 20, 2015.
Samuel Vozeh and Jean-Louis Steimer, Feedback Control Methods for Drug Dosage Optimisation, Concepts, Classification and Clinical Application, Clinical Pharmacokinetics, 10(6), pp. 457-476, Nov.-Dec. 1985.
Patent Abstracts of Japan, vol. 1999, No. 04, and JP 11 010036, Apr. 30, 1999 and Jan. 19, 1999, Toray Ind. Inc.
OmniPod Quick Start Guide, 2007, 2 pages.
OmniPod Insulin Management System-Investor Relations—Press Release, Feb. 1, 2005, http://investors.insulet.com/phoenix.zhtml?c=209336&p=irol-newsArticle&ID=988708&highlight= 1 page.
Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.
Medtronic News Release, "Medtronic Receives FDA Approval for World's First Insulin Pump with Real-time Continuous Glucose Monitoring," Apr. 13, 2006, 3 pages.
JDRF, Statistics: JDRF and Diabetes, http://jdrf.org/about-jdrf/facl-sheets/jdrf-anddiabetes-statistics/, 2014.
Hurley, Dan. Artificial Pancreas Makers Race to Market. Discover. Date published: Apr. 12, 2016. <http://discovermagazine.com/2016/may/13-priming-the-pump>.
Guy A. Dumont, Feedback Control for Clinicians, Springer Science+Media, Apr. 12, 2013, New York.
Fischer et al., In Vivo Comparison of Different Algorithms for the Artificial Beta-Cell, Artificial Organs, 9(2), International Society for Artificial Organs, May 1985, New York.
E. Salzsieder, G. Albrecht, E. Jutzi, and U. Fischer, Estimation of Individually Adapted Control Parameten for an Artificial Beta Cell, Biomedica Biochimica Acta. 43(5) pp. 585-596, May 1984.
Debiotech News Release, "Debiotech reveals its new miniaturized Disposable Insulin Nanopump™ for Diabetes therapy," available at http://www.debiotech.com/news/nw 159.html Apr. 24, 2006, 3 pages.
David A. Copp, Ravi Gondhalekar, and Joao P. Hespanha, Simultaneous Model Predictive Control and Moving Horizon Estimation for Blood Glucose Regulation in Type 1 Diabetes, Optimal Control Applications and Methods, Wiley InterScience, DOI: 10.1002/oca, pp. 1-15, Oct. 2016.
Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.
Collins and Lee, "Microfluidic flow transducer based on the measurement of electrical admittance," Lab Chip, 2004,4:7-10.
Centers for Disease Control and Prevention, Number (in Millions) of Adults with Diabetes by Diabetes Medication Status, United States, 1997-2011, http://www.cdc.gov/diabetes/statistics/meduse/fig1.him, 2013.
Bigfoot Biomedical Reveals its Automated Insulin Delivery System. diaTribe. Date published: Jan. 25, 2016 <https://diatribe.org/bigfoot-biomedical-reveals-its-automated-insulin-delivery-system>.
Bhalla, Raveesh, Understanding Material Design Part II, Sep. 28, 2014, Medium.com [online], [site visited Apr. 11, 2018], Available from Internet: https://medium.eom/@raveeshbhalla/understanding-material-design-cf2d60a16de3 (Year: 2014).
Accu-Chek Spirit, "Pump Therapy Made for You," Roche, 2006, 6 pages.
"Omnipod Horizon: Automated Glucose Control" Jun. 2017, 2 pages.
Written Opinion of the International Search Authority dated Oct. 22, 2018, for WO Application No. PCT/US18/042089, 9 pages.
International Search Report dated Oct. 22, 2018, for WO Application No. PCT/US18/042089,4 pages.

* cited by examiner

MULTI-SCALE DISPLAY OF BLOOD GLUCOSE INFORMATION

CROSS-REFERENCE TO RELATED APPLICATION

This application claims the benefit under 35 U.S.C. § 119(e) of U.S. Provisional Patent Application Ser. No. 62/532,168, filed Jul. 13, 2017, the disclosure of which is hereby incorporated herein in its entirety by this reference.

TECHNICAL FIELD

This document relates to a multi-scale display of blood glucose information and, more particularly, to the use of such a display in providing information regarding blood glucose levels of a person with diabetes (PWD).

BACKGROUND

People with Type I, Type II, or gestational diabetes must track their blood glucose levels and sometimes treat their condition to maintain appropriate blood glucose levels. Control of diabetes can include the monitoring of blood glucose levels using a blood glucose monitor (BGM) and sometimes a continuous glucose monitor (CGM). People with Type I, and some people with Type II or gestational diabetes, require insulin or an analog thereof. Because it cannot be taken orally, insulin is injected with a syringe or delivered subcutaneously by an external infusion pump. Excessive insulin delivery, however, can result in acute hypoglycemia, which can result in severe bodily injury and/or death. The failure to administer an appropriate amount of insulin to a person with diabetes, however, results in hyperglycemia, which can also result in severe bodily injury and/or death. Between the two conditions of hypoglycemia and hyperglycemia, hypoglycemia is more dangerous. Furthermore, dangerous levels of hypoglycemia are closer to normal levels than dangerous levels of hyperglycemia. Because of the risks involved, there is a need for an improved system for providing information regarding blood glucose levels.

The subject matter claimed in the present disclosure is not limited to embodiments that solve any disadvantages or that operate only in environments such as those described above. Rather, this background is only provided to illustrate one example of a technology area where some embodiments described in the present disclosure may be practiced.

BRIEF SUMMARY

Medication delivery systems, methods, and devices provided herein include at least a blood glucose monitor and/or monitoring device (e.g., a BGM, a CGM, etc.) and a display device (e.g., a smartphone having an installed app, tablet, personal computer, or wearable device having an installed app, an installed browser executing a browser application, an installed browser or app receiving information from a server, etc.). In some cases, the display device can serve as the primary user interface for providing blood glucose level information to a user. In some cases, the methods, devices, and systems provided herein can include an insulin delivery device (e.g., an insulin pump, a smart insulin pen, a connected dose-capture cap for an insulin pen, etc., and arranged, e.g., in an open-loop configuration, closed-loop configuration, or combinations thereof) in communication with or part of the blood glucose monitoring device and/or the display device. In some cases, the display device may be configured to monitor or otherwise obtain blood glucose levels and display those levels to a user of the device. For example, the display device may present the current blood glucose level on the display device based on a first scale, such as a logarithmic scale. The display device may display historical glucose levels on a second scale, such as a linear scale. In these and other embodiments, the second scale may be based on or anchored to the first scale. For example, the current blood glucose level may be displayed at a location based on a logarithmic scale along the vertical axis of the display, and the historical blood glucose levels may be displayed as a continuous line starting at the current blood glucose level using a linear scale. Thus, the display device may display the current blood glucose level according to a first scale and the historical blood glucose levels according to a second scale.

In some cases, the display device can project a future blood glucose level. The projected future blood glucose levels can also be displayed according to the second scale and anchored to the current blood glucose level presented based on the first scale. For example, the historic, current, and projected future blood glucose levels may all be displayed on a continuous line according to a linear scale. The location of the line along the vertical axis of the display device may be anchored to the location of the current blood glucose level based on a logarithmic scale.

One or more embodiments of the present disclosure may include a system for displaying blood glucose information that includes a blood glucose monitoring device configured to monitor blood glucose levels of a user, and a display. The system may also include one or more processors, and a non-transitory computer-readable medium containing instructions that, when executed by the one or more processors, cause the system to perform operations. The operations may include obtaining the blood glucose levels from the blood glucose monitoring device, where the blood glucose levels include at least a current blood glucose level and a historic blood glucose level. The operations may also include presenting the current blood glucose level at a first location on the display based on a first scale, and presenting the historic blood glucose level at a second location on the display based on a second scale different from the first scale.

One or more embodiments of the present disclosure may include a method of displaying blood glucose information. The method may include monitoring blood glucose levels of a user, where the blood glucose levels include at least a current blood glucose level and a historic blood glucose level. The method may also include presenting the current blood glucose level using a point indicator along an approximately horizontally centered axis based on a non-linear scale, and presenting the historic blood glucose level and a predicted future blood glucose level on the display as a single smoothed curve passing the point indicator.

The details of one or more implementations of various embodiments are set forth in the accompanying drawings and the description below. Other features, objects, and advantages of the various embodiments will be apparent from the description and drawings, and from the claims.

It is to be understood that both the foregoing general description and the following detailed description are merely examples and explanatory and are not restrictive of the claims.

BRIEF DESCRIPTION OF THE DRAWINGS

Example embodiments will be described and explained with additional specificity and detail through the use of the accompanying drawings in which.

DETAILED DESCRIPTION

Figure 1:
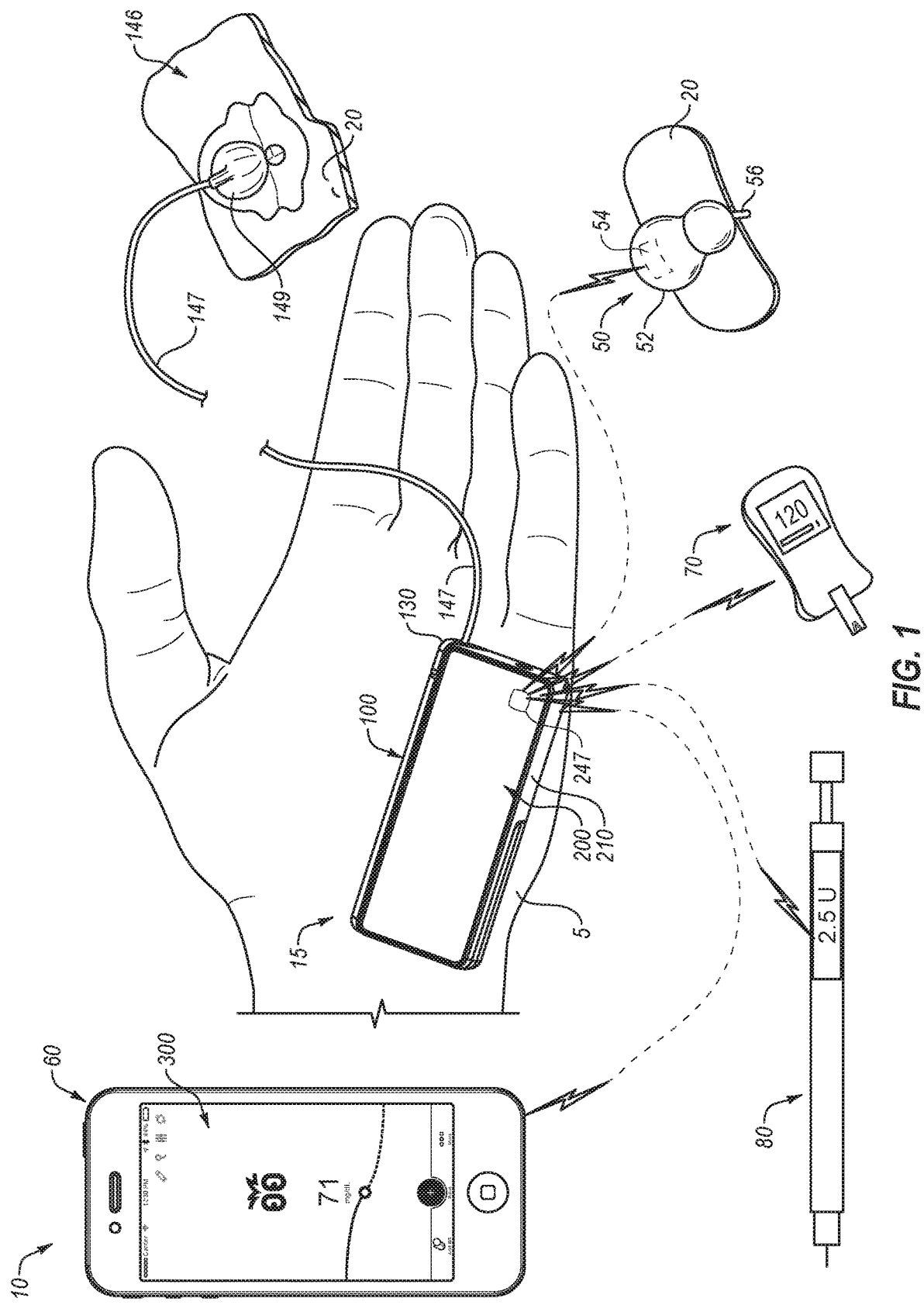
FIG. 1 provides an example system to display blood glucose information using multiple scales.

FIG. 1 provides an example system to display blood glucose information using multiple scales, in accordance with one or more embodiments of the present disclosure. The system of FIG. 1 may be described as a diabetes management system 10. The system 10 may include a pump assembly 15 for providing insulin and a continuous glucose monitor (CGM) 50. As shown, the continuous glucose monitor 50 is in wireless communication with pump assembly 15. In some cases, a continuous glucose monitor can be in wired communication with pump assembly 15. In some cases not shown, a continuous glucose monitor can be incorporated into an insulin pump assembly. As shown, pump assembly 15 can include a reusable pump controller 200 that forms part of the pump assembly 15. In some cases, reusable pump controller 200 is adapted to determine one or more basal delivery rates. In some cases, continuous glucose monitor 50 can act as a controller adapted to communicate basal delivery rates to pump assembly 15.

Pump assembly 15, as shown, can include reusable pump controller 200 and a disposable pump 100, which can contain a reservoir for retaining insulin. A drive system for pushing insulin out of the reservoir can be included in either the disposable pump 100 or the reusable pump controller 200 in a controller housing 210. Reusable pump controller 200 can include a wireless communication device 247, which can be adapted to communicate with a wireless communication device 54 of continuous glucose monitor 50 and other diabetes devices in the system, such as those discussed below. In some cases, pump assembly 15 can be sized to fit within a palm of a hand 5. Pump assembly 15 can include an infusion set 146. Infusion set 146 can include a flexible tube 147 that extends from the disposable pump 100 to a subcutaneous cannula 149 that may be retained by a skin adhesive patch (not shown) that secures the subcutaneous cannula 149 to the infusion site. The skin adhesive patch can retain the subcutaneous cannula 149 in fluid communication with the tissue or vasculature of the PWD so that the medicine dispensed through flexible tube 147 passes through the subcutaneous cannula 149 and into the PWD's body. A cap device 130 can provide fluid communication between an output end of an insulin cartridge (not shown) and flexible tube 147 of infusion set 146. Although pump assembly 15 is depicted as a two-part insulin pump, one piece insulin pumps are also contemplated. Additionally, insulin pump assemblies used in methods and systems provided herein can alternatively be a patch pump.

Continuous glucose monitor 50 (e.g., a glucose monitoring device) can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of the PWD's blood glucose level or the like. In some cases, the sensor shaft 56 can measure glucose or another analyte in interstitial fluid or in another fluid and correlate that to blood glucose levels. In response to the measurements made by the sensor shaft 56, the continuous glucose monitor 50 can employ the wireless communication device 54 to transmit data to a corresponding wireless communication device 247 housed in the pump assembly 15. In some cases, the continuous glucose monitor 50 may include a circuit that permits sensor signals (e.g., data from the sensor shaft 56) to be communicated to the wireless communication device 54. The wireless communication device 54 can transfer the collected data to reusable pump controller 200 (e.g., by wireless communication to the wireless communication device 247). Additionally or alternatively, the diabetes management system 10 may include another glucose monitoring device that may utilize any of a variety of methods of obtaining information indicative of a PWD's blood glucose levels and transferring that information to reusable pump controller 200. For example, an alternative monitoring device may employ a micropore system in which a laser porator creates tiny holes in the uppermost layer of a PWD's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. In other examples, the monitoring device can include detect glucose levels using equilibrium fluorescence detectors (e.g., sensors including a diboronic acid receptor attached to a fluorophore). Furthermore, it should be understood that in some alternative implementations, continuous glucose monitor 50 can be in communication with reusable pump controller 200 or another computing device via a wired connection. In some cases, continuous glucose monitor 50 can be adapted to provide blood glucose measurements for a PWD when in use for the PWD at regular or irregular time intervals. In some cases, continuous glucose monitor 50 can detect blood glucose measurements at least every thirty minutes, at least every fifteen minutes, at least every ten minutes, at least every five minutes, or about every minute. In some cases, continuous glucose monitor 50 can itself determine a basal delivery rate using methods provided herein and communicate that basal rate to the pump assembly 15. In some cases, continuous glucose monitor 50 can transmit blood glucose measurement data to reusable pump controller 200 and reusable pump controller 200 can use methods provided herein to determine a basal delivery rate. In some cases, a remote controller can receive glucose data from continuous glucose monitor 50, determine a basal delivery rate using methods provided herein, and communicate the basal rate to pump assembly 15.

Diabetes management system 10 may optionally include a blood glucose meter 70 (e.g., a glucose sensor). In some cases, blood glucose meter 70 can be in wireless communication with reusable pump controller 200. Blood glucose meter 70 can take a blood glucose measurement using one or more test strips (e.g., blood test strips). A test strip can be inserted into a strip reader portion of the blood glucose meter 70 and then receive the PWD's blood to determine a blood glucose level for the PWD. In some cases, the blood glucose meter 70 is configured to analyze the characteristics of the PWD's blood and communicate (e.g., via a BLUETOOTH® wireless communication connection) the information to reusable pump controller 200. In some cases, a user can manually input a glucose meter reading. The blood glucose meter 70 can be manually operated by a user and may include an output subsystem (e.g., display, speaker) that can provide the user with blood glucose readings that can be subsequently entered into the reusable pump controller 200 or user interface to collect the data from an unconnected BGM into the system. The blood glucose meter 70 may be configured to communicate data (e.g., blood glucose readings) obtained to reusable pump controller 200 and/or other devices, such as a display device 60 (e.g., a control device). Such communication can be over a wired and/or wireless connection, and the data can be used by system 10 for a number of functions (e.g., calibrating the continuous glucose monitor 50, confirming a reading from the continuous glucose monitor 50, determining a more accurate blood glucose reading for a bolus calculation, detecting a blood glucose level when the continuous glucose monitor 50 is malfunctioning).

In some cases, the diabetes management system 10 can further include a display device 60 that can communicate with the reusable pump controller 200 through a wireless and/or wired connection with the reusable pump controller 200 (e.g., via a BLUETOOTH® wireless communication connection or a near-field communication connection). In some cases, the display device 60 communicates wirelessly with other diabetes devices of system 10. The display device 60 can be any of a variety of appropriate computing devices, such as a smartphone, a tablet computing device, a wearable computing device, a smartwatch, a fitness tracker, a laptop computer, a desktop computer, and/or other appropriate computing devices. In some cases (for example, where the reusable pump controller 200 does not determine a basal delivery rate), the display device 60 can receive and log data from other elements of the system 10 and determine basal delivery rates using any method or approach, for example, selecting a basal delivery rate or a number of basal delivery rates that produce lowest cost function values, and any method or approach described in U.S. Patent Publication 2017/0332952, published Nov. 23, 2017 and entitled "INSULIN DELIVERY SYSTEM AND METHODS WITH RISK BASED SET POINTS" (hereinafter "Desborough"), the entire contents and disclosure of which are hereby incorporated herein by this reference. In some cases, the basal delivery rate may be based at least in part on projected blood glucose levels. For example, the display device 60 may predict future blood glucose levels based on historical readings, current JOB, expected delivery rate, etc. The display device may project and/or predict future blood glucose levels in any predictive manner, including the example set forth below and/or as set forth in Desborough.

Example Techniques for Predicting Future Blood Glucose Values

Systems and methods provided herein can use any suitable physiology model to predict future blood glucose values (represented as $BG_t$ and $\gamma_t$). In some cases, methods and systems provided herein can predict future blood glucose values using past and current carbohydrate, insulin, and blood glucose values.

Systems and methods provided herein can in some cases estimate a first future blood glucose a model. In some cases, blood glucose can be approximated using two determinist Integrating first order plus dead time (FOPDT) models for the effect of carbohydrates and insulin, combined with an autoregressive (AR2) disturbance model. Accordingly, blood glucose (BG) at time (t) can be estimated using the following equation:

$$BG_t = y_t = BGc_t + BGi_t + BGd_t = G_c C_t + G_i i_t + G_d e^{\alpha_t}$$

From the equation above, the first element may represent the effect on blood glucose due to carbohydrates:

$$G_c = \frac{K_c(1-\alpha_c)B^{C_{dt}}}{(1-\alpha_c B)(1-B)}$$

where:
B is the backward shift operator such that $B\gamma_t = \gamma_{t-1}$, $B^2\gamma_t = \gamma_{t-2}$, $B^k\gamma_t = \gamma_{t-k}$ $$k_c = \frac{ISF}{CR}$$

is the carb gain (in units of mg/dl/g)

$$\alpha_c = e^{-\frac{ts}{\tau_c}},$$

where $\tau_c$ is the carb time constant (for example, approximately 30 minutes), and
where ts is the sampling time (for example, a CGM may use a sampling time interval of every 5 minutes),
$c_{dt} = \text{floor}(\tau_{dc}/ts)$, where $\tau_{dc}$ is the carb deadtime (for example, approximately 15 minutes)

From the equation above, the second element may represent the effect on blood glucose due to insulin:

$$G_i = \frac{K_i(1-\alpha_c)B^{i_{dt}}}{(1-\alpha_i B)(1-B)}$$

where:
$k_i = -ISF$ is the insulin gain (in units of mg/dl/unit), $$\alpha_i = e^{-\frac{ts}{\tau_i}},$$

where $\tau_i$ is the insulin time constant (for example, approximately 120 minutes),
$i_{dt} = \text{floor}(\tau_{di}/ts)$, where $\tau_{di}$ is the insulin deadtime (for example, approximately 30 minutes), From the equation above, the third element may represent the effect on blood glucose due to disturbances (e.g., the AR2 disturbance model):
$G_d e^{\alpha_t}$
and may be based on the following log-transformed AR2 model:

$$\ln\left(\frac{BGd_t}{\mu^*}\right) = \alpha_1 \ln\left(\frac{BGd_{t-1}}{\mu^*}\right) + \alpha_2 \ln\left(\frac{BGd_{t-2}}{\mu^*}\right) + \alpha_t$$

which when rearranged, yields:

$$BGd_t = BGd_{t-1}^{\alpha_1} BGd_{t-2}^{\alpha_2} \mu^{*(1-\alpha_1-\alpha_2)} e^{\alpha_t}$$

where, in some examples, $$a_t \sim \text{Normal}(0, \sigma_a)$$

and $$\sigma_a \approx 50\% \ \ln(\sigma^*)\sqrt{\frac{1+\alpha_2}{1-\alpha_2}((1-\alpha_2)^2)-\alpha_1^2)} \text{ with}$$

$$\mu^* \sim 10^{\text{Normal}(2.09,\, 0.08)} \text{ and } \sigma^* \sim 10^{\text{Normal}(0.15,\, 0.028)} \text{ such that}$$

$$\alpha_1 \approx 1.6442, \ \alpha_2 \approx 0.6493.$$

Using the above notation, expansion of the initial equation for $BG_t$ may be represented by the equation:

$$BG_t = \frac{k_c(1-\alpha_c)}{(1-\alpha_c B)(1-B)} c_{t-dt_c} +$$

$$\frac{k_i(1-\alpha_i)}{(1-\alpha_i B)(1-B)} i_{t-dt_i} + BGd_{t-1}^{\alpha_1} BGd_{t-2}^{\alpha_2} \mu^{*(1-\alpha_1-\alpha_2)}$$

Systems and methods provided herein can in some cases calculate an amount of insulin on board (IOB) and/or an amount of carbohydrates on board (COB) in order to predict future blood glucose values. IOB and COB represent the amount of insulin and carbohydrates, respectively, which have been infused and/or consumed but not yet metabolized. Knowledge of IOB and COB can be useful for a user of a method or system provided herein when it comes to bolus decisions to prevent insulin stacking, but knowledge of IOB and COB can also be used in methods and systems provided herein to predict future blood glucose values.

IOB and COB represent the amount of insulin and carbohydrates, respectively, which have been infused and/or consumed but not yet metabolized. Knowledge of IOB can be useful in correcting bolus decisions to prevent insulin stacking. Knowledge of IOB and COB can be useful for predicting and controlling blood glucose. Both insulin infusion and carbohydrate consumption can involve deadtime or transportation delay (e.g., it can take ten to forty minutes for insulin and/or carbohydrates to begin to affect blood glucose). During the period immediately after entering the body (e.g., during the deadtime period), it can be beneficial to account for IOB and COB in any decisions such as bolusing. This can be called "Decision" IOB/COB. "Action" IOB/COB, on the other hand, can represent the insulin and/or carbohydrates available for action on blood glucose. In some cases, Decision IOB can be a displayed IOB, while Action IOB can be an IOB determined for use in selecting a basal delivery rate or profile in methods and systems provided herein.

From the equations above, $$BG_{it} = \frac{-ISF(1-\alpha_i)B^{i_{dt}}}{(1-\alpha_i B)(1-B)} i_{t-i_{dt}}$$

where $$BY_t = Y_{t-1},\ B^2 Y_t = Y_{t-2},\ B^k Y_t = Y_{t-k}$$

$$\alpha_i = e^{-\frac{ts}{\tau_i}}$$

where $\tau_i$ is the insulin time constant (for example, approximately 120 minutes) $i_{dt}=\text{floor}(\tau_{di}/\text{ts})$, where $\tau_{di}$ is the insulin deadtime (for example, approximately 30 minutes) and where ts is the sampling time (for example, a CGM may use a sampling time interval of every 5 minutes)

"Decision" IOB

In some embodiments, Decision IOB at time (t) ($IOB\_D_t$) may be calculated according to the following mathematical process:

$$IOB\_D_t = IOB\_D_{t-1} - \frac{BGi_t - BGi_{t-1}}{-ISF} + i_t \text{ or, alternatively,}$$

$$\nabla IOB\_D_t = -\frac{\nabla BGi_t}{-ISF} + i_t$$

substituting the equation above for $BG_{it}$ into the equation for $IOB\_D_t$ or $\nabla IOB\_D_t$ yields $$IOB_{Dt} = \frac{1-\alpha_i B - (1-\alpha_i)B^i dt}{1-(\alpha_i+1)B+\alpha_i B^2} i_t \text{ or, alternatively,}$$

$$\nabla IOB\_D_t = -\frac{1-\alpha_i}{1-\alpha_i B} i_{t-dt} + i_t$$

"Action" IOB

In some embodiments, Action IOB at time (t) ($IOB\_A_t$) may be calculated according to the following mathematical process:

$$IOB\_A_t = \frac{1}{1-\alpha_i B} i_{t-i_{dt}}$$

For an arbitrary series of insulin infusions, using an infinite series of expansions of $$\frac{1}{1-\alpha_i B},$$

$IOB\_A_t$ may be represented by $$IOB_{A_t} = \sum_{k=0}^{n} \alpha_i^k i_{t-k-i_{dt}}$$

Stated another way, $$BGi_t = \frac{-ISF(1-\alpha_i)}{1-B} IOB\_A_t$$

The formulas for COB, including Action COB and Decision COB, may be developed in a similar fashion, using the equation above related to $G_c$:

$$G_{ct} = \frac{k_c(1-\alpha_c)B^{c_{dt}}}{(1-\alpha_c B)(1-B)}$$

Accordingly, future blood glucose data can be estimated using current or recent blood glucose data, data about when carbohydrates were consumed, and/or data regarding when insulin was and/or will be administered. Moreover, because evaluated insulin delivery profiles and/or rates include basal insulin delivery rates above and below the BBR, those insulin delivery rates above BBR can be added to the IOB calculation and insulin delivery rates below the BBR can be subtracted from the IOB. In some cases, a variation in a Decision IOB due to actual variations from BBR can be limited to positive deviations in order to prevent a user from entering an excessive bolus.

In some cases, a user can input relevant data into the display device 60. In some cases, the display device 60 can be used to transfer data from the reusable pump controller 200 to another computing device (e.g., a back-end server or a cloud-based device). In some cases, the display device 60 provides a user interface (e.g., graphical user interface (GUI), speech-based user interface, motion-controlled user interface) through which users can provide information to control operation of the reusable pump controller 200 and the diabetes management system 10. For example, the display device 60 can be a mobile computing device running a mobile app that communicates with reusable pump controller 200 over short-range wireless connections (e.g., BLUETOOTH® connection, Wi-Fi Direct connection, near-field communication connection, etc.) to provide status information for the system 10 and allow a user to control operation of the system 10 (e.g., toggle between delivery modes, adjust settings, log food intake, change a fear of hypoglycemia index (FHI), confirm/modify/cancel bolus dosages, and the like).

By way of further characterization, a GUI typically includes one or more information regions and active/activatable regions. As used in this disclosure, an information region is a region of a GUI which presents information to a user. An activatable region is a region of a GUI, such as a button, slider, or a menu, which allows the user to take some action with respect to the GUI (e.g., if manipulated, such as with a point-and-click interface, a touch interface, an audio interface, etc.). Some information regions are also activatable regions in that they present information and enable some action that may be taken by a user. Activatable regions may be displayed as GUI elements/objects, for example, buttons, sliders, selectable panes, menus, etc., all of various shapes and sizes.

Generally, if an interaction is detected by a GUI, a process is used to determine the activatable regions of the GUI to which the contact corresponds, if any. For example, if a touch is detected at an "ENTER", then responsive to the detected touch a process may determine that the contact was at the ENTER button. The ENTER button is an activatable region, so one or more events may be created at the GUI and/or an underlying application that invoked the GUI.

Optionally, diabetes management system 10 may include a bolus administering device 80 (e.g., a syringe, an insulin pen, a smart syringe with device communication capabilities, or the like) through which bolus dosages can be manually administered to a PWD. In some cases, a suggested dosage for a bolus to be administered using the bolus administering device 80 can be output to a user via the user interface of reusable pump controller 200 and/or the user interface of the display device 60. In some cases, the bolus administering device 80 can communicate through a wired and/or wireless connection with reusable pump controller 200 and/or the display device 60. In some cases, system 10 can allow users to input insulin deliveries made using a syringe or insulin pen.

In some cases, the display device 60 includes a display 300. The display device 60 can display blood glucose information. For example, the display device 60 may obtain blood glucose readings from the CGM 50 or the blood glucose meter 70. The display device 60 may store the blood glucose readings as historic blood glucose readings and the most recent blood glucose level as the current blood glucose level. The display device 60 may display various aspects of the blood glucose levels and/or projected blood glucose levels as explained in greater detail below.

While one embodiment of a diabetes management system is illustrated in FIG. 1, it will be appreciated that any number, type, or style of diabetes management devices may be utilized in conjunction with the present disclosure. For example, a patch pump, a syringe, etc., may be utilized to enter doses of insulin delivered to a PWD. As another example, any blood glucose reading device may be utilized, such as a BGM, a CGM, a flash glucose monitor (FGM), or any other blood glucose reading device. In some embodiments, an insulin delivery device may not be used.

Modifications, additions, or omissions may be made to FIG. 1 without departing from the scope of the present disclosure. For example, the diabetes management system 10 may include any type or style of insulin delivery devices and/or monitoring devices. As another example, the display device 60 may take any form or style of computing device. As an additional example, the display device 60 may be coupled with a remote cloud device (not illustrated) that may store one or more aspects of the monitored and/or projected blood glucose levels and/or insulin delivery rates and/or projections. Such a cloud device may be accessible by a third party (e.g., a physician) or a PWD.

Figure 2:
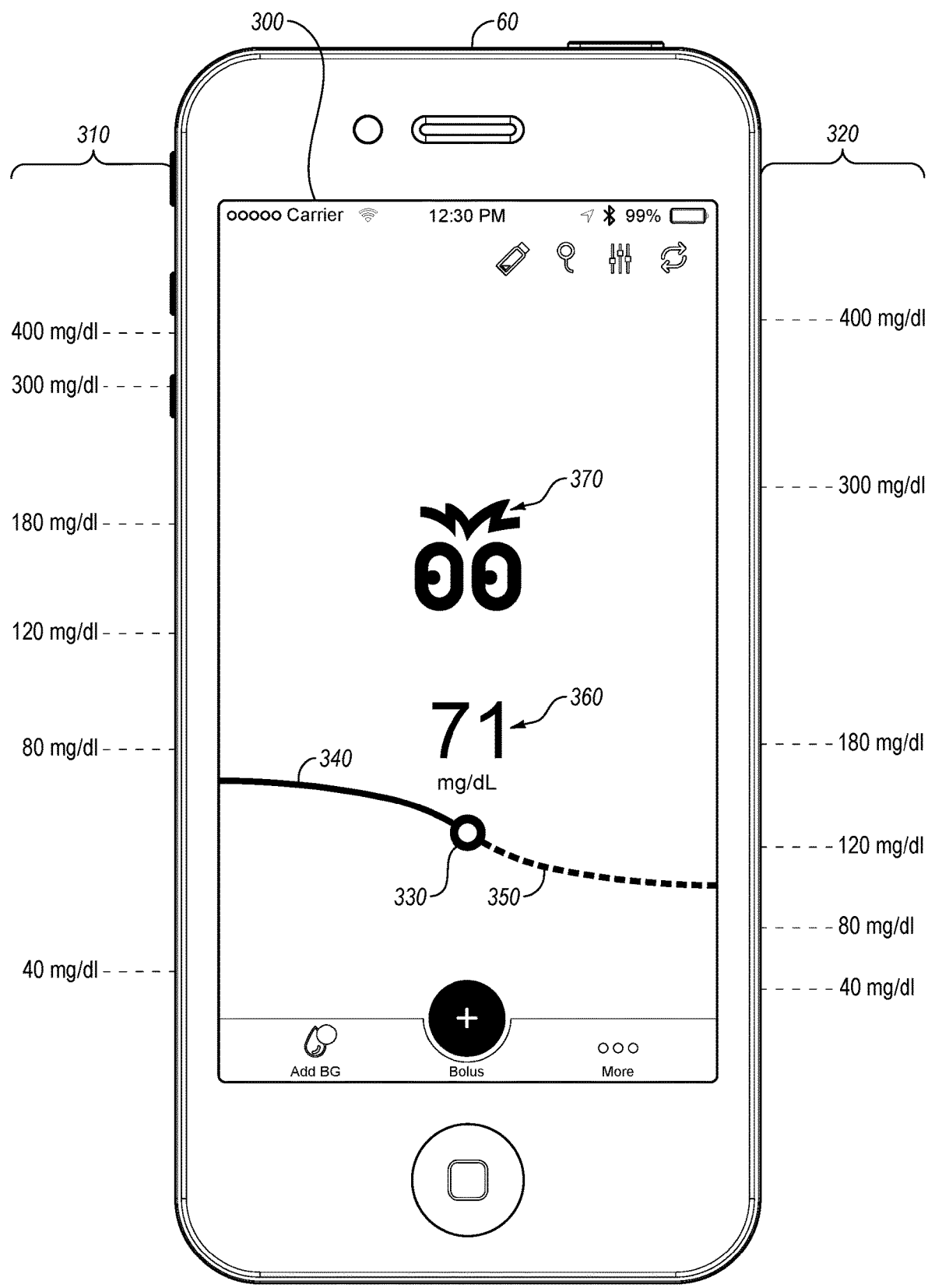
FIG. 2 is an example display of blood glucose information using multiple scales.

FIG. 2 is an example display 300 of blood glucose information using multiple scales, in accordance with one or more embodiments of the present disclosure. The display 300 may be part of the display device 60 of FIG. 1. The display 300 may present blood glucose information based on a first scale 310 and a second scale 320. In some cases, the display 300 may present a current blood glucose level 330, historical blood glucose levels 340, and projected blood glucose levels 350. Additionally or alternatively, the display 300 may include a numerical representation 360 of the current blood glucose level 330 and/or an avatar 370 for a glanceable view of blood glucose information.

In some embodiments, the blood glucose information may be displayed on the display 300 using both the first scale 310 and the second scale 320. As illustrated in FIG. 2, the first scale 310 may be a risk-based scale such that areas of greater risk may receive more of the total space of the display 300. For example, the risk of blood glucose levels of a PWD going below normal blood glucose levels (e.g., hypoglycemia) may be more severe than the risks of a PWD going above normal blood glucose levels (e.g., hyperglycemia). Using a risk-based scale, blood glucose levels corresponding to hypoglycemia may cover a larger portion of the display 300 than other scales.

The first scale 310 may include a logarithmic scale such that lower values receive logarithmically more space of the display 300. For example, as illustrated in FIG. 2, according to the first scale 310, the range from 400 mg/dL to 180 mg/dL may cover approximately 35% of the display 300 used for blood glucose information, the range from 180 mg/dL to 80 mg/dL may cover approximately 35% of the display 300 used for blood glucose information, and the range from 80 mg/dL to 40 mg/dL may cover approximately 30% of the display 300 used for blood glucose information.

The second scale 320 may illustrate a linear scale that also covers the display 300 used for displaying blood glucose information. For example, as illustrated in FIG. 2, according to the second scale 320, the range from 400 mg/dL to 180 mg/dL covers approximately 61% of the display 300 used for blood glucose information, the range from 180 mg/dL to 80 mg/dL covers approximately 28% of the display 300 used for blood glucose information, and the range from 80 mg/dL to 40 mg/dL covers approximately 11% of the display 300 used for blood glucose information. In these and other embodiments, the second scale 320 may provide a framework within which various aspects of blood glucose information may be displayed. Intuitively, some users such as PWDs may more readily understand and relate to a linear scale (such as the second scale 320) as opposed to a logarithmic scale (such as the first scale 310).

In some embodiments, the current blood glucose level 330 may be displayed based on the first scale 310. For example, an icon, marker, or other indication of the current blood glucose level 330 may be displayed along a vertical axis of the display 300 based on the logarithmic first scale 310. In some embodiments, the current blood glucose level 330 may be displayed at approximately the center of the display 300 along a horizontal axis of the display 300. Additionally or alternatively, the current blood glucose level 330 may move along a vertical axis along the center of the horizontal axis as changes occur in the current blood glucose level 330.

In some cases, the current blood glucose level 330 may be based on a BGM, a CGM, an FGM, or any other blood glucose monitoring device. In these and other cases, "current" blood glucose levels may include the most recent blood glucose reading, a blood glucose reading within a time threshold (e.g., within the last 1 minute, within the last 2 minutes, within the last 5 minutes, within the last 10 minutes, within the last 15 minutes, etc.), or combinations thereof. In some embodiments, an icon representing the current blood glucose level 330 may change based on how recent the latest reading has been taken. For example, the color of the icon may fade over time, or the icon may no longer be present after a certain duration of time, etc.

In some embodiments, the historical blood glucose levels 340 and/or the projected blood glucose levels 350 may be displayed according to the second scale 320. In some embodiments, the second scale 320 may be anchored or oriented based on the first scale 310. Examples, of such anchoring may be explained in greater detail with reference to FIGS. 3 and/or 4. The second scale 320 may be displayed in FIG. 2 to illustrate variations in the amount of the display 300 covered by various spans of blood glucose levels according to the first scale 310 and the second scale 320.

By displaying blood glucose information using the first scale 310, a greater visual distinction is observable for hypoglycemic ranges as compared to the second scale 320. Furthermore, using the first scale 310, the range of 300-400 mg/dL (which is rarely used) only uses approximately 10% of the display 300 rather than over 25% of the display 300 when using the second scale 320.

Figure 6A:
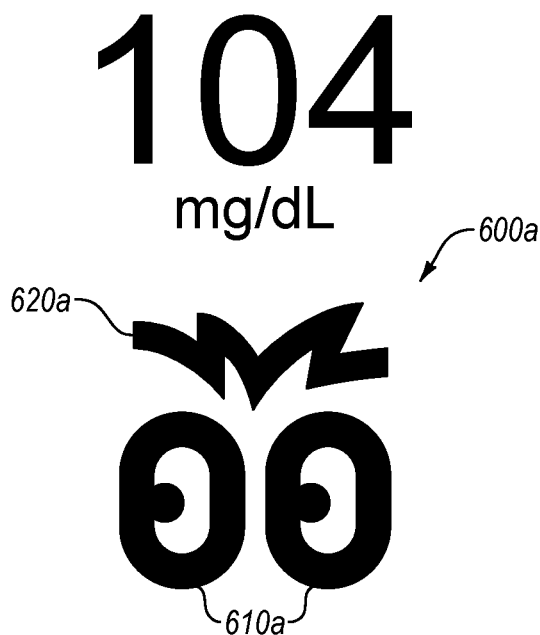
FIGS. 6A and 6B illustrate example features of a display of blood glucose information.

The avatar 370 for glanceability may be described with greater detail with reference to FIGS. 6A and/or 6B.

Figure 3A:
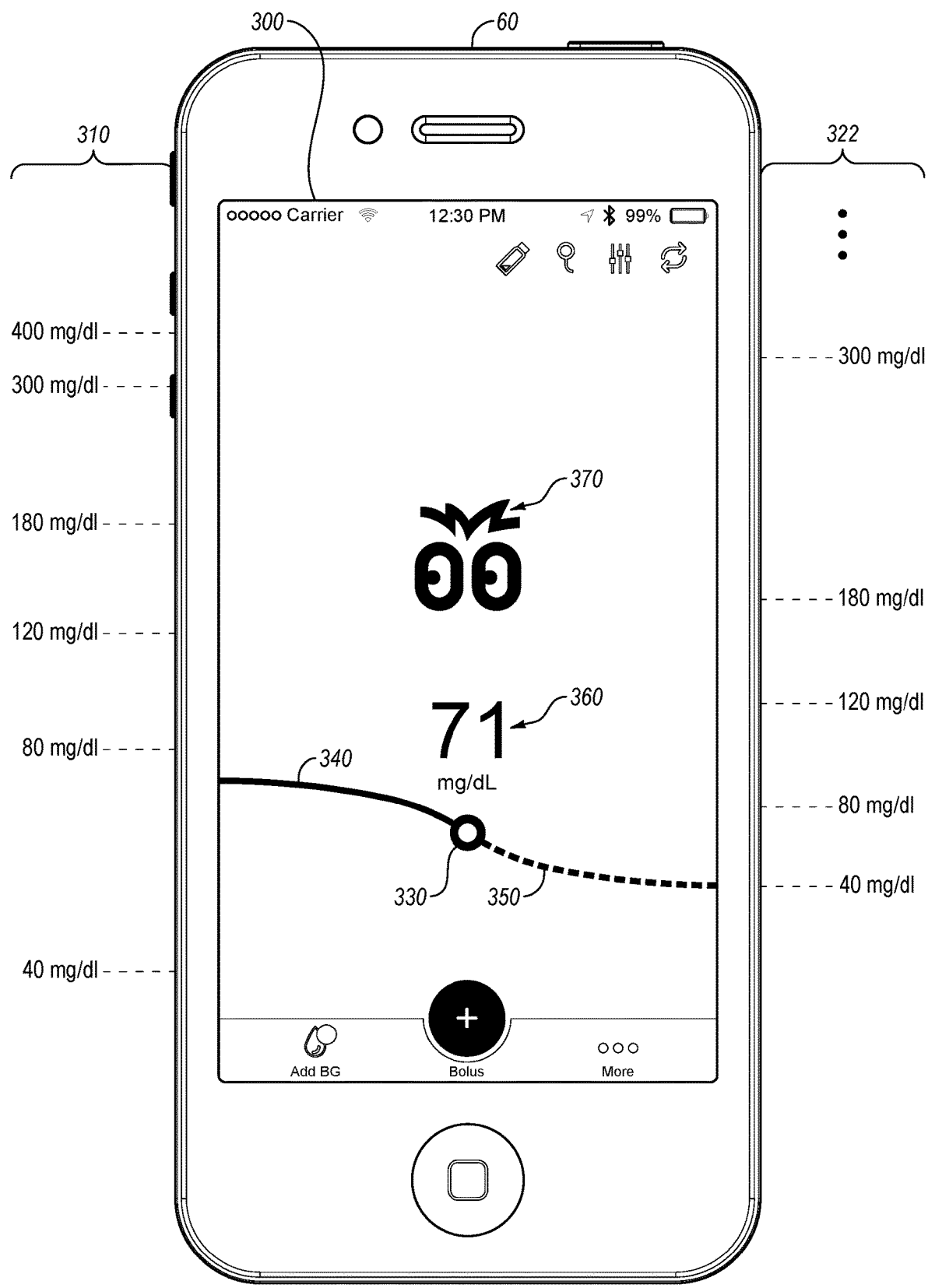
FIGS. 3A and 3B are other example displays of blood glucose information using multiple scales.
Figure 3B:
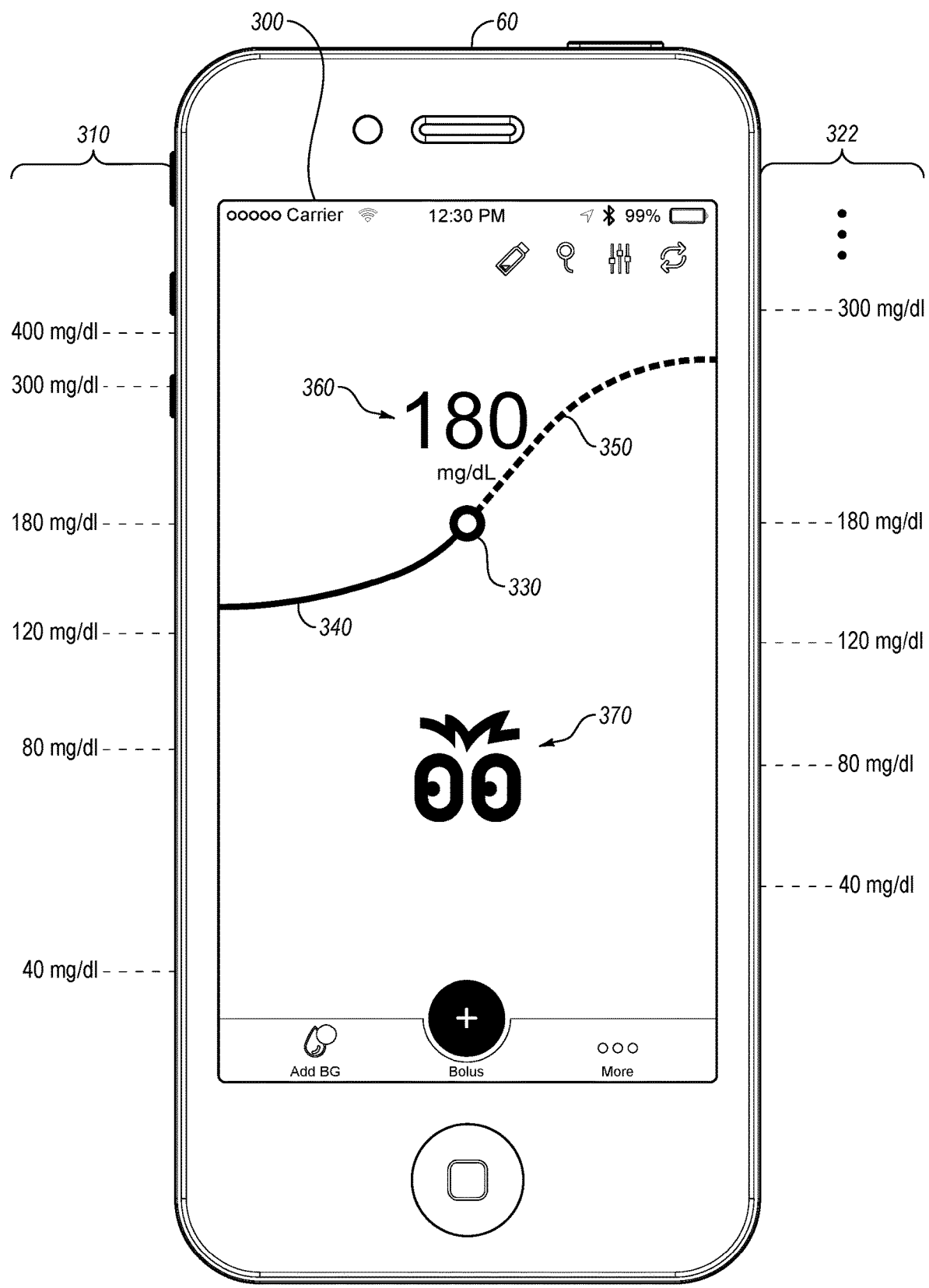

FIGS. 3A and 3B are other example displays 300 of blood glucose information using multiple scales, in accordance with one or more embodiments of the present disclosure. FIGS. 3A and 3B are similar to FIG. 2, with the variation that a second scale 322 is anchored differently than in FIG. 2.

As illustrated in FIGS. 3A and 3B, the second scale 322 may be anchored along the vertical axis of the display 300 based on the location of the current blood glucose level 330 based on the first scale 310. For example, the current blood glucose level 330 illustrated in FIG. 3A is approximately 71 mg/dL. The second scale 322 may be shifted along the vertical axis of the display 300 such that the current blood glucose level 330, located along the vertical axis in the first scale 310, is also at the same vertical position along the vertical axis of the display 300. The second scale 322 may be anchored in the vertical axis based on the current blood glucose level 330 according to the first scale 310. As another example, as illustrated in FIG. 3B, the current blood glucose level 330 is approximately 180 mg/dL, and the second scale 322 is anchored to that value according to the first scale 310.

As illustrated in FIG. 3A, the current blood glucose level 330 of 71 mg/dL may be displayed along the vertical axis of the display 300 according to the first scale 310. The historical blood glucose levels 340 may be displayed relative to the current blood glucose level 330 according to the second scale 322. For example, a continuous line from 71 mg/dL may proceed back in time up to approximately 85 mg/dL on the second scale 322 (while if the first scale 310 were used the historical blood glucose levels 340 would indicate only approximately 75 mg/dL). As another example, a continuous line from 71 mg/dL may proceed forward in time down to approximately 40 mg/dL for the projected blood glucose levels 350 according to the second scale 322 (while if the first scale 310 were used the projected blood glucose levels 350 would only be approximately 55 mg/dL). In one embodiment, the continuous line may comprise visual indicators to show that a part of the continuous line corresponds to historical, current, and projected blood glucose levels. For example, in FIG. 3A, historical blood glucose levels 340 are shown as a solid line, current blood glucose levels 330 is shown as circle that defines a white space, and projected blood glucose levels 350 are shown as a dashed line.

In some cases, the historical blood glucose levels 340 may be smoothed in the display 300. For example, the historical blood glucose levels 340 may follow a line that is smoothed to follow a curved, rather than a jagged line. Additionally or alternatively, extrapolation may be performed on blood glucose levels in between points of actual readings to facilitate smoothing of the historical blood glucose levels 340.

In some cases, the historical blood glucose levels 340 may be corrected based on an updated and/or corrected current blood glucose level 330. For example, if a newly calibrated blood glucose monitoring device provides a current blood glucose level 330 different than what is expected from the historic readings before the calibration of the device, the historical readings may be corrected based on the updated current blood glucose level 330 to smooth the historical blood glucose levels 340.

Using such an approach, the benefit of the risk-based scale may be utilized in displaying the current blood glucose level 330 along the vertical axis of the display 300. For example, hypoglycemic blood glucose levels have a larger area of the display 300 than with a linear scale such that a PWD will have a greater visual cue of how close to hypoglycemic levels they are approaching. Additionally, by using the second scale 322 for the historical blood glucose levels 340 and/or the projected blood glucose levels 350, a PWD may be able to observe trends according to a scale with which they are more familiar or comfortable and/or that may be more intuitive to the PWD.

In some cases, the future blood glucose levels 350 and/or the historical blood glucose levels 340 may be displayed as a sparkline. For example, the future blood glucose levels 350 may be displayed without a specific scale or without a specific numerical indication of the future blood glucose levels 350. Using such an embodiment, a PWD may be provided with a sense of the direction of their future blood glucose levels 350 without being overly focused on the exact levels. Additionally or alternatively, such a sparkline may be smoothed such that no clear data points are evidenced by a sudden change in direction of the line, but rather illustrate trends. Such a sparkline may provide glanceability where a PWD may glance at the display 300 and recognize generally what their historic blood glucose levels have been (e.g., low/high) and what their predicted blood glucose levels are expected to be (e.g., trending low/high) without being overloaded with data.

In some cases, an interface of the display 300 may be invoked to view a more detailed graph of the blood glucose levels conveyed by the sparkline. For example, a PWD may swipe down on the sparkline to view a more detailed graph that includes specific data points, axis labels, numerical indicators, reference lines, trend lines, and/or any other graph feature to provide a PWD a more detailed view into historic, current, and/or future blood glucose levels.

In some cases, a background color or colors may be utilized to improve glanceability. For example, a region above the line and/or a region below the line of the historical blood glucose levels 340, current blood glucose level 330, and future blood glucose levels 350 may vary based on blood glucose levels. Such an approach can give a PWD a rapid indication of blood glucose levels. For example, the color and/or color change can be based on a threshold (e.g., 180 mg/dL (or 200 or 250 or 300) for hyperglycemic blood glucose levels and 80 mg/dL (or 70 or 50 or 40) for hypoglycemic blood glucose levels). In some cases, the color may be based on the currentblood glucose level 330. Additionally or alternatively, the color and/or color change may be basedon future blood glucose levels 350. In some cases the region below the line may be based on thecurrent blood glucose levels 330 and the region above the line may be based on the future blood glucose levels 350, or vice versa. In some cases, the color change can be an instant color change, or can based on a gradient shift as the blood glucose level changes. For example, if a PWD has a current blood glucose level of 100 mg/dL the color may be gray, and as the current blood glucose level drops below 80 mg/dL, the color may change from gray to blue. As another example, if the current blood glucose level is 160 mg/dL with a projected future blood glucose level trending up to 250 mg/dL, the color may be gray and transitioning to red such that as the projected blood glucose levels cross the threshold, the color is red. In some cases, the color yellow can be used to indicate hyperglycemia, blue can be used to indicate euglycemia, and red can be used to indicate hypoglycemia. Any color scheme may be used.

Figure 4:
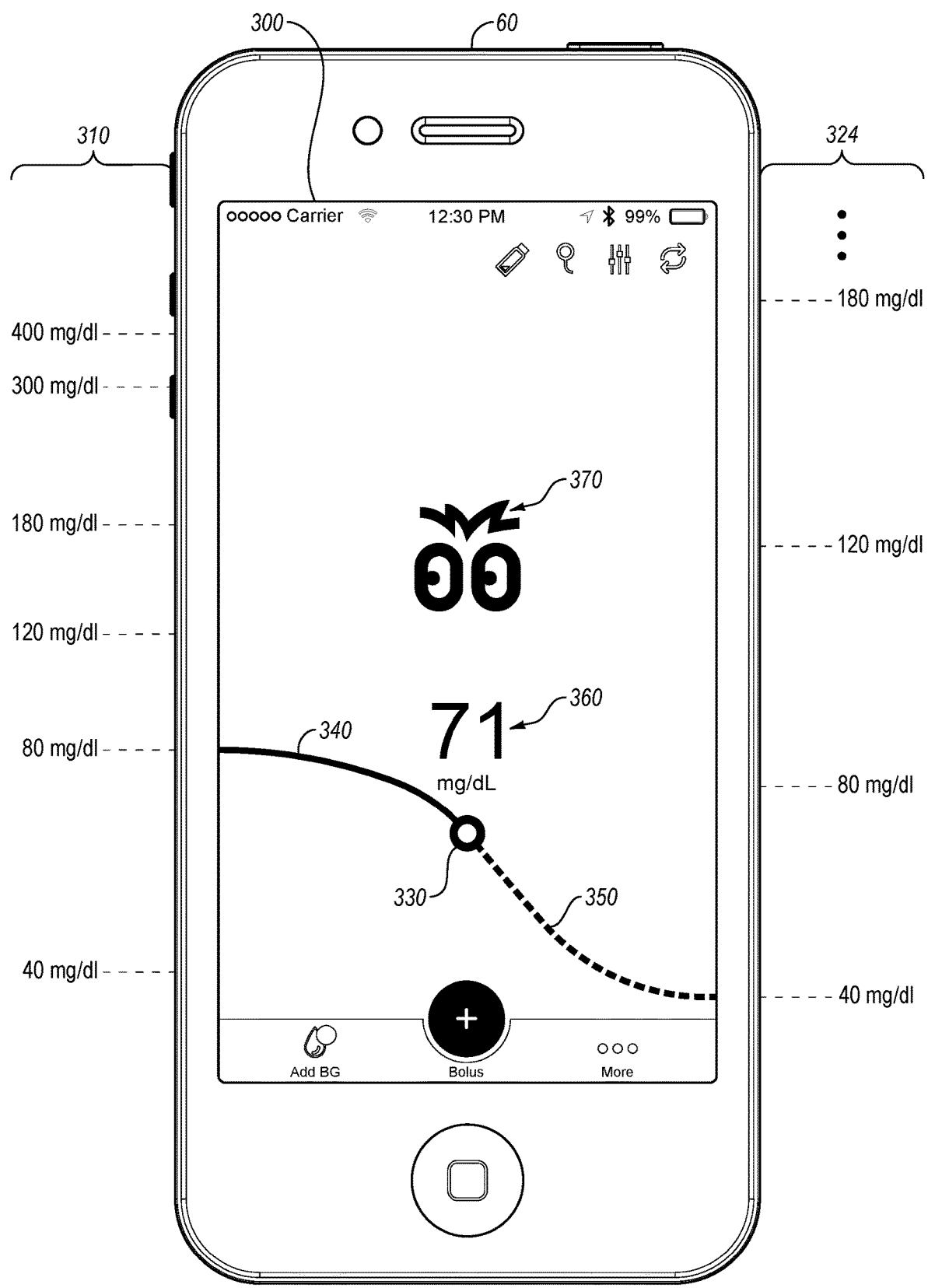
FIG. 4 is an additional example display of blood glucose information using multiple scales.

FIG. 4 is an additional example display 300 of blood glucose information using multiple scales, in accordance with one or more embodiments of the present disclosure. FIG. 4 is similar to FIGS. 3A and 3B except the second scale 324 of FIG. 4 is made larger than the second scale 322 of FIGS. 3A and 3B, while still being a linear scale and still anchored based on the first scale 310.

As illustrated in FIG. 4, the second scale 324 may be made larger such that changes in blood glucose levels and trends thereof may be more readily observed. For example, the historical blood glucose levels 340, the current blood glucose level 330, and the future blood glucose levels 350 may span from 85 mg/dL to 40 mg/dL and cover approximately 25% of the space of the display 300 based on the second scale 324. In FIGS. 3A and 3B, the same range covers approximately 12% of the display 300.

Modifications, additions, or omissions may be made to FIGS. 2-4 without departing from the scope of the present disclosure. For example, the display 300 may include numerical markings along the vertical axis of the display indicating the first scale and/or the second scale. As another example, the first scale may be any scale to emphasize certain regions of potential blood glucose levels. As an additional example, the second scale may be any magnification of the linear scale.

Figure 5:
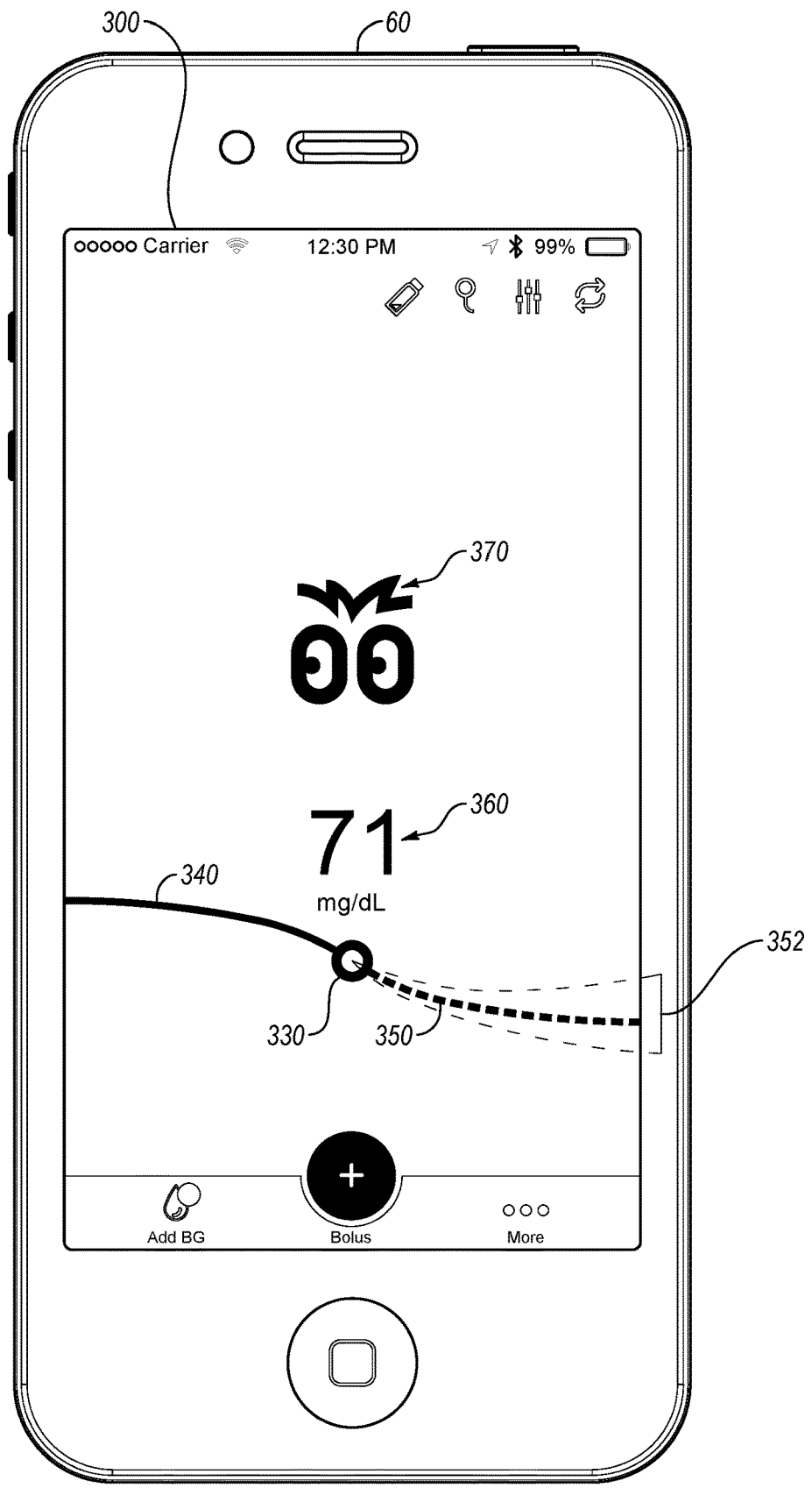
FIG. 5 is another example display of blood glucose information using multiple scales.

FIG. 5 is another example display 300 of blood glucose information using multiple scales. As illustrated in FIG. 5, in some embodiments, the projected blood glucose levels 350 may include a feature to illustrate a level of confidence in the projected blood glucose levels 350.

Depending on the approach used to project the future blood glucose levels, different future blood glucose levels may have different levels of confidence in the accuracy of the projected blood glucose levels. In some embodiments, as the projected blood glucose levels go further into the future, the confidence levels may decrease (e.g., the accuracy of the projected blood glucose level may be less and less sure).

In some embodiments, the level of confidence may be illustrated by a range 352 of potential future blood glucose levels. For example, the range 352 may illustrate that the projected future blood glucose levels close to the current blood glucose level 330 may be only a small range of values, and as the projected blood glucose levels go further into the future, the range 352 increases. The level of confidence may be illustrated in any manner, such as by error bars, maximum and/or minimum values, color changes, transparency, etc.

Modifications, additions, or omissions may be made to FIG. 5 without departing from the scope of the present disclosure. For example, the display 300 may include any approach to display confidence levels of the projected blood glucose levels.

Figure 6B:
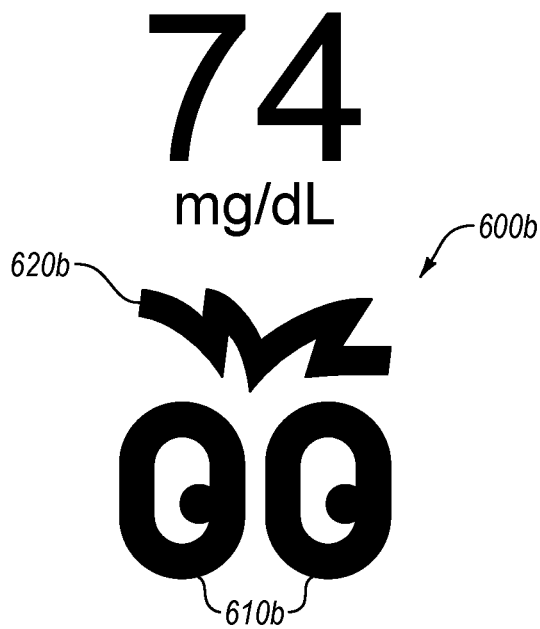

FIGS. 6A and 6B illustrate example features of a display of blood glucose information, in accordance with one or more embodiments of the present disclosure. For example, FIG. 6A illustrates a first avatar 600a and FIG. 6B illustrates a second avatar 600b. The first avatar 600a and the second avatar 600b may correspond to the same PWD but at different points in time.

The first avatar 600a may include features to facilitate glanceability (which may be further characterized as "glanceable," and means understandable at a glance or with occasional glances) regarding blood glucose information and/or operation of a diabetes management system (such as the system 10 of FIG. 1). In some embodiments, the first avatar 600a may include a facial avatar with various features of the first avatar 600a associated with various blood glucose information and/or aspects of the operation of the diabetes management system.

In some embodiments, the eyes 610a may represent the current blood glucose information. For example, whether the pupils of the eyes 610a are on the left or the right of the eyeballs may indicate whether the current blood glucose level is above or below a threshold. As another example, the pupils of the eyes 610a may be at an approximate location along the vertical length of the eyeball correlated with the vertical length of a display (such as the display 300).

In some embodiments, the eyebrows 620a may represent trends of historical and/or projected blood glucose levels.

For example, if the historical blood glucose levels were higher than the current blood glucose level, the left side of the eyebrows 620*a* may be tilted in an upward direction and if the historical blood glucose levels were lower than the current blood glucose level, the left side of the eyebrows 620*a* may be tilted in a downward or lower direction. As another example, if the trend of the projected blood glucose levels are approximately the same as the current blood glucose levels, the right side of the eyebrows 620*a* may be relatively level. Alternatively, if the trend of the projected blood glucose levels are higher than the current blood glucose level, the right side of the eyebrows 620*a* may be curved upwards. 0089

In some embodiments, a color of the avatar may shift and/or change based on blood glucose information and/or operation of the diabetes management system. For example, if the PWD is projected to have low blood sugar level below a threshold or the current blood glucose level is below a threshold, the coloration of the avatar may change to a warning color such as red. As another example, if the PWD is trending toward higher blood glucose levels, the tone of the color of the first avatar 600*a* may get lighter and if trending toward lower blood glucose levels, the tone of the color of the first avatar 600*a* may get darker. In some cases, the color change may be a background shading of the first avatar 600*a* and may change in a similar manner as described for the background color. For example, the color, shade, etc., of the first avatar 600*a* may change based on whether a blood glucose level is hyperglycemic, euglycemic, or hypoglycemic.

FIG. 6B provides an illustration of changes from the first avatar 600*a* to second avatar 600*b* as the blood glucose level transitions from 104 mg/dL to 74 mg/dL. For example, eyebrows 620*b* of the second avatar 600*b* are raised on the left, indicating that the historical values (e.g., 104 mg/dL) are higher than the present value. As another example, the pupils of the eyes 610*b* may transition to the right side of the eyeball as the blood glucose level may have dropped below a threshold value.

While described in terms of blood glucose information, any aspect of blood glucose information and/or operation of the diabetes management system is contemplated. For example, a feature of the first avatar 600*a* may correspond to whether or not the diabetes management system is providing personalized basal insulin delivery. As another example, a feature of the avatar may be related to whether or not there is an error or malfunction in the diabetes management system 10, such as an occlusion in an insulin pump.

Modifications, additions, or omissions may be made to FIGS. 6A and 6B without departing from the scope of the present disclosure. For example, the first and/or second avatars 600*a*, 600*b* may be correlated with any aspect of blood glucose information and/or any aspect of operation of the diabetes management system. As another example, while illustrated as a facial avatar, any multi-component image or avatar may be used.

Figure 7:
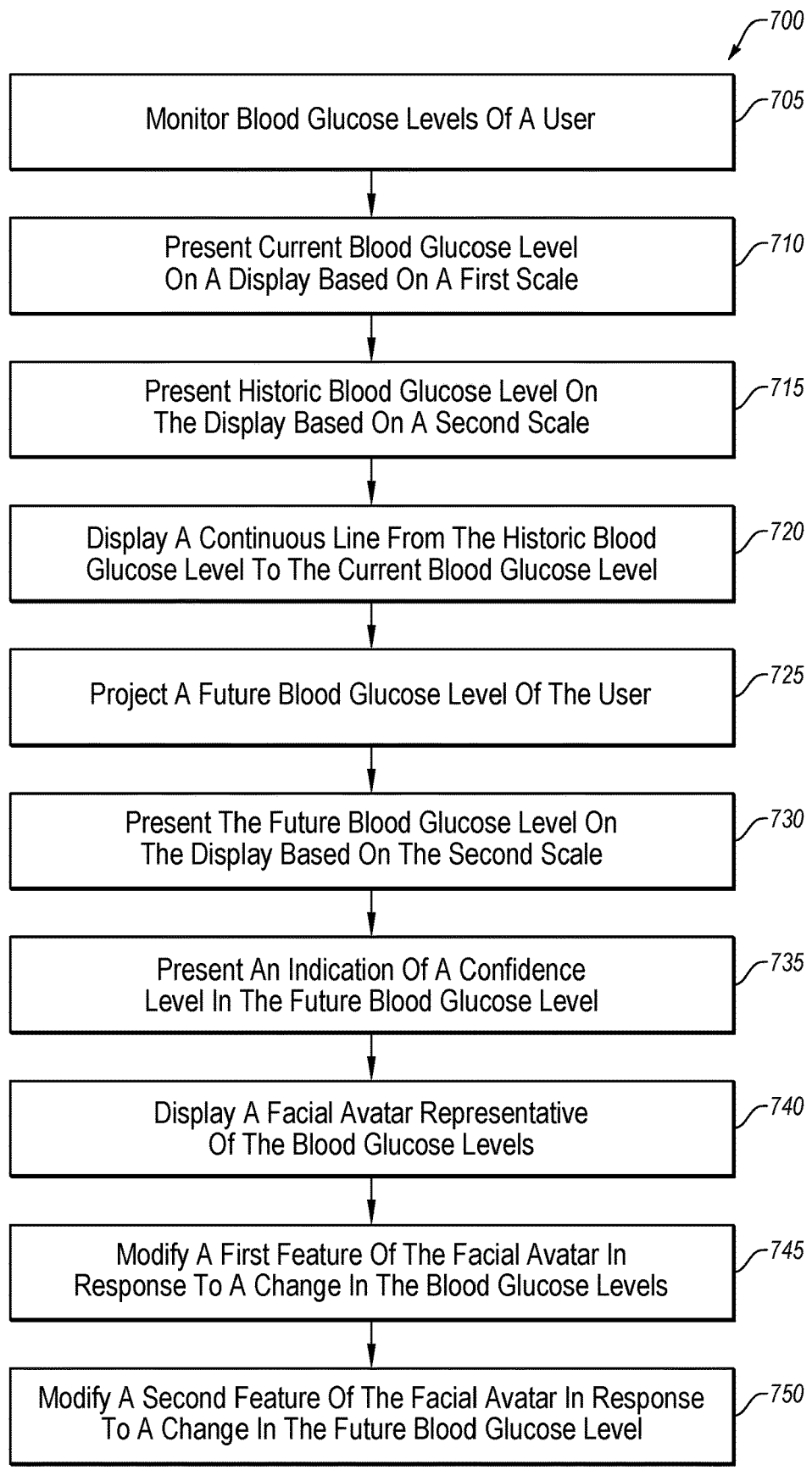
FIG. 7 illustrates a flowchart of an example method of displaying blood glucose information using multiple scales.

FIG. 7 illustrates a flow diagram of an example method 700 of presenting blood glucose information using multiple scales. The method 700 may be performed by any suitable system, apparatus, or device. For example, the diabetes management system 10, the pump assembly 15, the display device 60 of FIG. 1, and/or a remote server may perform one or more of the operations associated with the method 700. Although illustrated with discrete blocks, the steps and operations associated with one or more of the blocks of the method 700 may be divided into additional blocks, combined into fewer blocks, or eliminated, depending on the desired implementation.

At block 705, blood glucose levels may be monitored for a PWD. For example, a diabetes management system (such as the system 10 of FIG. 1) may monitor the blood glucose levels using a CGM and/or a BGM. In these and other embodiments, a single device may monitor the blood glucose levels or a separate device may obtain the blood glucose levels from a monitoring device.

At block 710, a current blood glucose level may be presented on a display based on a first scale. For example, the current blood glucose level may be displayed at a first location along the vertical axis of the display based on a first scale, such as a risk-based scale. The risk-based scale may include a logarithmic scale.

At block 715, historic blood glucose levels may be presented on the display based on a second scale. For example, the historic blood glucose levels may be displayed at a second location based on the second scale and the location of the current blood glucose level. For example, the second scale may be anchored to the location of the current blood glucose level. The second scale may include a linear scale.

At block 720, a continuous line may be displayed from the current blood glucose level to one or more of the historic blood glucose levels. For example, a line may be extrapolated between the current blood glucose level and a historic level such that a continuous line may be displayed.

At block 725, a future blood glucose level of the user may be projected.

At block 730, the projected future blood glucose level of the block 725 may be presented on the display based on the second scale. For example, the future blood glucose level may be presented according to the same scale as the historic blood glucose levels. Additionally or alternatively, a continuous line may be displayed connecting the future blood glucose level and the current blood glucose level.

At block 735, an indication of a confidence level in the future blood glucose level may be presented.

At block 740, a facial avatar representative of the blood glucose levels may be displayed. Additionally or alternatively, another type of avatar or other multi-feature image may be displayed.

At block 745, a first feature of the facial avatar may be modified in response to a change in the blood glucose levels. For example, based on a newly received blood glucose level the first feature may be modified. As another example, the first feature may be modified based on changes to trends in blood glucose levels (e.g., based on historical blood glucose levels).

At block 750, a second feature of the facial avatar may be modified in response to a change in the future blood glucose level. For example, the second feature may be modified based on a trend associated with the future blood glucose level or a projected blood glucose level.

Modifications, additions, or omissions may be made to the method 700 without departing from the scope of the present disclosure. For example, the operations of the method 700 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer-readable storage media including Random-Access Memory (RAM), Read-Only Memory (ROM), Electrically Erasable Programmable Read-Only Memory (EEPROM), Compact Disc Read-Only Memory (CD-ROM) or other optical disc storage, magnetic disk storage or other magnetic storage devices, Flash memory devices (e.g., solid state memory devices), or any other storage medium that may be used to carry or store desired program code in the form of computer-executable instructions or data structures and which may be accessed by a general-purpose or special-purpose computer. Combinations of the above may also be included within the scope of computer-readable media.

Computer-executable instructions comprise, for example, instructions and data which cause a general-purpose computer, special-purpose computer, or special-purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general-purpose hardware (e.g., computer-readable media, processing devices, etc.) of the computing system. In some embodiments, the different components, modules, engines, and services described herein may be implemented as objects or processes that execute on the computing system (e.g., as separate threads). Routines and operations performed by a processor, machine-readable instructions that a processor executes to perform such routines and operations, and functions that such routines and operations enable, may be described herein as an "algorithm" or a number of related "algorithms." While some of the system and methods described herein are generally described as being implemented in software (stored on and/or executed by general-purpose hardware), specific hardware implementations or a combination of software and specific hardware implementations are also possible and contemplated. In the present description, a "computing entity" may be any computing system as previously defined herein, or any module or combination of modulates running on a computing system.

Any ranges expressed herein (including in the claims) are considered to be given their broadest possible interpretation. For example, unless explicitly mentioned otherwise, ranges are to include their end points (e.g., a range of "between X and Y" would include X and Y). Additionally, ranges described using the terms "approximately" or "about" are to be understood to be given their broadest meaning consistent with the understanding of those skilled in the art. Additionally, the term approximately includes anything within 10%, or 5%, or within manufacturing or typical tolerances.

All examples and conditional language recited herein are intended for pedagogical objects to aid the reader in understanding the disclosure and the concepts contributed by the inventor to furthering the art and are to be construed as being without limitation to such specifically recited examples and conditions. Although embodiments of the present disclosure have been described in detail, it should be understood that the various changes, substitutions, and alterations could be made hereto without departing from the spirit and scope of the disclosure.

Additional non-limiting embodiments of the disclosure include:

Embodiment 1. A method of displaying blood glucose information, the method comprising: monitoring blood glucose levels of a user, the blood glucose levels including at least a current blood glucose level and a historic blood glucose level; presenting the current blood glucose level using a point indicator along an approximately horizontally centered axis based on a non-linear scale; and presenting the historic blood glucose level and a predicted future blood glucose level on the display as a single smoothed curve passing the point indicator.

Embodiment 2. The method of Embodiment 1, wherein the display includes a first color above the single smoothed curve and a different second color below the single smoothed curve.

Embodiment 3. The method of Embodiment 1 or Embodiment 2, changing the first color, the second color, or both based on the current blood glucose level.

Embodiment 4. The method of one of Embodiments 1-3, plotting the single smoothed curve on a linear scale anchored on the display based on the current blood glucose level plotted on the non-linear scale.

Embodiment 5. The method of one of Embodiments 1-4, wherein the smoothed curve provides a non-numerical representation of the predicted future blood glucose level.

Embodiment 6. The method of one of Embodiments 1-5, predicting a future blood glucose level using a predictive algorithm that uses insulin delivery and/or food consumption data.

Embodiment 7. The method of Embodiment 6, wherein the predictive algorithm assumes a future basal insulin delivery that is adjusted based on a closed-loop insulin delivery algorithm.

Embodiment 8. The method of Embodiment 1, wherein the smoothed curve and/or the point indicator provide an approximation of the predicted future blood glucose level.

Embodiment 9. The method of Embodiment 1, further comprising: presenting a blood glucose level representation that corresponds to the first non-linear scale, and wherein the presented predicted future blood glucose level is presented relative to the blood glucose level representation.

Embodiment 10. The method of Embodiment 9, wherein the blood glucose level representation comprises one or more of numerical representations of blood glucose levels and non-numerical representations of blood glucose levels.

Embodiment 11. The method of Embodiment 10, wherein the blood glucose level representation comprises at least one region defined by a first numerical representation of a blood glucose level and a second numerical representation of a blood glucose level, and at least part of the presented predicted future blood glucose level corresponds the at least one region.

Embodiment 12. A device for displaying blood glucose information, comprising: a display; one or more processors;

and a non-transitory computer-readable medium containing instructions that, when executed by the one or more processors, cause the device to perform operations, the operations comprising: monitoring blood glucose levels of a user, the blood glucose levels including at least a current blood glucose level and a historic blood glucose level; presenting the current blood glucose level using a point indicator along an approximately horizontally centered axis based on a non-linear scale; and presenting the historic blood glucose level and a predicted future blood glucose level on the display as a single smoothed curve passing the point indicator.

Embodiment 13. The device of Embodiment 12, wherein the display includes a first color above the single smoothed curve and a different second color below the single smoothed curve.

Embodiment 14. The device of Embodiment 12 or Embodiment 13, wherein the operations further comprise changing the first color, the second color, or both based on the current blood glucose level.

Embodiment 15. The device of one of Embodiments 12-14, wherein the operations further comprise plotting the single smoothed curve on a linear scale anchored on the display based on the current blood glucose level plotted on the non-linear scale.

Embodiment 16. The device of one of Embodiments 12-15, wherein the smoothed curve is configured to provide a non-numerical representation of the predicted future blood glucose level.

Embodiment 17. The device of one of Embodiments 12-16, wherein the operations further comprise predicting a future blood glucose level using a predictive algorithm that uses insulin delivery and/or food consumption data.

Embodiment 18. The device of Embodiment 17, wherein the predictive algorithm assumes a future basal insulin delivery that is adjusted based on a closed-loop insulin delivery algorithm.

Embodiment 19. The device of one of Embodiments 12-18, wherein the smoothed curve and/or the point indicator provide an approximation of the predicted future blood glucose level.

Embodiment 20. The device of one of Embodiments 12-19, wherein the operations further comprise:
presenting a blood glucose level representation that corresponds to the first non-linear scale, and wherein the presented predicted future blood glucose level is presented relative to the blood glucose level representation.

Embodiment 21. The device of one of Embodiments 12 to 20, wherein the blood glucose level representation comprises one or more of numerical representations of blood glucose levels and non-numerical representations of blood glucose levels.

Embodiment 22. The device of one of Embodiments 12 to 21, wherein the blood glucose level representation comprises at least one region defined by a first numerical representation of a blood glucose level and a second numerical representation of a blood glucose level, and at least part of the presented predicted future blood glucose level corresponds the at least one region.

What is claimed is:

1. A method of displaying blood glucose information, the method comprising:
monitoring blood glucose levels of a user, the blood glucose levels including at least a current blood glucose level and a historic blood glucose level;
presenting the current blood glucose level using a point indicator centered on a horizontal axis, wherein the point indicator is displayed according to a non-linear vertical scale of blood glucose levels; and
presenting the historic blood glucose level and a predicted future blood glucose level on a display as a single smoothed curve passing through the point indicator, wherein the historic blood glucose level and the predicted future blood glucose level are displayed according to a linear vertical scale of blood glucose levels.

2. The method of claim 1, wherein the display includes a first color above the single smoothed curve and a different second color below the single smoothed curve.

3. The method of claim 2, changing the first color, the different second color, or both based on the current blood glucose level.

4. The method of claim 1, wherein the linear vertical scale of blood glucose values is anchored on the display based on the current blood glucose level plotted on the non-linear vertical scale of blood glucose values.

5. The method of claim 1, wherein the single smoothed curve provides a non-numerical representation of the predicted future blood glucose level.

6. The method of claim 1, predicting a future blood glucose level using a predictive algorithm that uses insulin delivery and/or food consumption data.

7. The method of claim 6, wherein the predictive algorithm assumes a future basal insulin delivery that is adjusted based on a closed-loop insulin delivery algorithm.

8. The method of claim 1, wherein the smoothed curve and/or the point indicator provide an approximation of the predicted future blood glucose level.

9. The method of claim 1, further comprising:
presenting a blood glucose level representation that corresponds to the non-linear vertical scale of blood glucose levels, and
wherein the presented predicted future blood glucose level is presented relative to the blood glucose level representation.

10. The method of claim 9, wherein the blood glucose level representation comprises one or more of numerical representations of blood glucose levels and non-numerical representations of blood glucose levels.

11. The method of claim 10, wherein the blood glucose level representation comprises at least one region defined by a first numerical representation of a blood glucose level and a second numerical representation of a blood glucose level, and at least part of the presented predicted future blood glucose level corresponds to the at least one region.

12. A device for displaying blood glucose information, comprising:
a display;
one or more processors; and
a non-transitory computer-readable medium containing instructions that, when executed by the one or more processors, cause the device to perform operations, the operations comprising:
monitoring blood glucose levels of a user, the blood glucose levels including at least a current blood glucose level and a historic blood glucose level;
presenting the current blood glucose level using a point indicator centered on a horizontal axis, wherein the point indicator is displayed according to a non-linear vertical scale of blood glucose levels; and
presenting the historic blood glucose level and a predicted future blood glucose level on the display as a single smoothed curve passing through the point indicator wherein the historic blood glucose level and the predicted future blood glucose level are displayed according to a linear vertical scale of blood glucose levels.

13. The device of claim 12, wherein the display includes a first color above the single smoothed curve and a different second color below the single smoothed curve.

14. The device of claim 13, wherein the operations further comprise changing the first color, the different second color, or both based on the current blood glucose level.

15. The device of claim 12, wherein the linear vertical scale of blood glucose values is anchored on the display based on the current blood glucose level plotted on the non-linear vertical scale of blood glucose values.

16. The device of claim 12, wherein the single smoothed curve is configured to provide a non-numerical representation of the predicted future blood glucose level.

17. The device of claim 12, wherein the operations further comprise predicting a future blood glucose level using a predictive algorithm that uses insulin delivery and/or food consumption data.

18. The device of claim 17, wherein the predictive algorithm assumes a future basal insulin delivery that is adjusted based on a closed-loop insulin delivery algorithm.

19. The device of claim 12, wherein the smoothed curve and/or the point indicator provide an approximation of the predicted future blood glucose level.

20. The device of claim 12, wherein the operations further comprise:
presenting a blood glucose level representation that corresponds to the non-linear vertical scale of blood glucose levels, and
wherein the presented predicted future blood glucose level is presented relative to the blood glucose level representation.

21. The device of claim 20, wherein the blood glucose level representation comprises one or more of numerical representations of blood glucose levels and non-numerical representations of blood glucose levels.

22. The device of claim 21, wherein the blood glucose level representation comprises at least one region defined by a first numerical representation of a blood glucose level and a second numerical representation of a blood glucose level, and at least part of the presented predicted future blood glucose level corresponds to the at least one region.

* * * * *

UNITED STATES PATENT AND TRADEMARK OFFICE
CERTIFICATE OF CORRECTION

| | | |
|---|---|---|
| PATENT NO. | : 11,389,088 B2 | |
| APPLICATION NO. | : 16/035230 | |
| DATED | : July 19, 2022 | |
| INVENTOR(S) | : Lane Desborough et al. | |

It is certified that error appears in the above-identified patent and that said Letters Patent is hereby corrected as shown below:

In the Specification

| | | |
|---|---|---|
| Column 5, | Line 51, | change "JOB" to --IOB-- |
| Column 13, | Line 37, | change "currentblood" to --current blood-- |
| Column 13, | Line 39, | change "basedon" to --based on-- |
| Column 13, | Line 40, | change "thecurrent" to --the current-- |
| Column 15, | Line 13, | delete "0089" |

Signed and Sealed this
Eleventh Day of April, 2023

Katherine Kelly Vidal
*Director of the United States Patent and Trademark Office*